US012162912B2

(12) United States Patent
Kennedy et al.

(10) Patent No.: US 12,162,912 B2
(45) Date of Patent: Dec. 10, 2024

(54) PROTEINS FOR BLOCKING NEUROTRANSMITTER RELEASE

(71) Applicant: THE REGENTS OF THE UNIVERSITY OF COLORADO, A BODY CORPORATE, Denver, CO (US)

(72) Inventors: Matthew Kennedy, Denver, CO (US); Chandra Tucker, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 743 days.

(21) Appl. No.: 17/295,736

(22) PCT Filed: Nov. 21, 2019

(86) PCT No.: PCT/US2019/062620
§ 371 (c)(1),
(2) Date: May 20, 2021

(87) PCT Pub. No.: WO2020/106962
PCT Pub. Date: May 28, 2020

(65) Prior Publication Data

US 2022/0017577 A1 Jan. 20, 2022

Related U.S. Application Data

(60) Provisional application No. 62/770,520, filed on Nov. 21, 2018.

(51) Int. Cl.
*C07K 14/33* (2006.01)
*A61K 38/00* (2006.01)
(Continued)

(52) U.S. Cl.
CPC ................ *C07K 14/33* (2013.01); *C12N 9/52* (2013.01); *C12N 15/62* (2013.01); *A61K 38/00* (2013.01); *C12Y 304/24069* (2013.01)

(58) Field of Classification Search
CPC .......... C07K 14/33; C12N 9/52; C12N 15/62; A61K 38/00; C12Y 304/24069
See application file for complete search history.

(56) References Cited

U.S. PATENT DOCUMENTS

2007/0161067 A1 7/2007 Gambhir et al.
2014/0056870 A1 2/2014 James et al.

FOREIGN PATENT DOCUMENTS

WO 2000/061192 A2 10/2000
WO 2002/008268 A2 1/2002
WO WO-2017220800 A1 * 12/2017 ......... A61K 31/7105

OTHER PUBLICATIONS

UniProt Q9R631_CLOBO; https://www.uniprot.org/uniprotkb/Q9R631/entry; accessed Jan. 2, 2024 (Year: 2000).*
(Continued)

*Primary Examiner* — Louise W Humphrey
*Assistant Examiner* — Candice Lee Swift
(74) *Attorney, Agent, or Firm* — Saul Ewing LLP; Kathryn Doyle; Domingos J. Silva

(57) ABSTRACT

The present invention includes light-controlled and light-independent neurotoxin systems and methods for using such neurotoxin systems for rapidly and locally silencing distinct populations of neurons.

13 Claims, 16 Drawing Sheets
Specification includes a Sequence Listing.

(51) Int. Cl.
 C12N 9/52 (2006.01)
 C12N 15/62 (2006.01)

(56) References Cited

OTHER PUBLICATIONS

Brunger, Axel T., et al. "Botulinum neurotoxin heavy chain belt as an intramolecular chaperone for the light chain." PLoS pathogens 3.9 (2007): e113. (Year: 2007).*

C9WWY7_CLOBO; https://www.uniprot.org/uniprotkb/C9WWY7/ entry; accessed Jan. 3, 2023 (Year: 2009).*

Kennedy, Matthew J., et al. "Rapid blue-light-mediated induction of protein interactions in living cells." Nature methods 7.12 (2010): 973-975. (Year: 2010).*

Kakumoto, Toshiyuki, and Takao Nakata. "Optogenetic control of PIP3: PIP3 is sufficient to induce the actin-based active part of growth cones and is regulated via endocytosis." PloS one 8.8 (2013): e70861. (Year: 2013).*

Ueda, Yoshibumi. "The role of phosphoinositides in synapse function." Molecular neurobiology 50.3 (2014): 821-838. (Year: 2014).*

Zimmerman, Seth P., et al. "Tuning the binding affinities and reversion kinetics of a light inducible dimer allows control of transmembrane protein localization." Biochemistry 55.37 (2016): 5264-5271. (Year: 2016).*

Liu, Qi, and Chandra L. Tucker. "Engineering genetically-encoded tools for optogenetic control of protein activity." Current opinion in chemical biology 40 (2017): 17-23. (Year: 2017).*

Rost, Benjamin R., et al. "Optogenetic tools for subcellular applications in neuroscience." Neuron 96.3 (2017): 572-603. (Year: 2017).*

Takayama, Kazuo, and Hiroyuki Mizuguchi. "Generation of optogenetically modified adenovirus vector for spatiotemporally controllable gene therapy." ACS chemical biology 13.2 (2018): 449-454. (Year: 2018).*

Lin, John Y., et al. "Optogenetic inhibition of synaptic release with chromophore-assisted light inactivation (CALI)." Neuron 79.2 (2013): 241-253. (Year: 2013).*

"Extended European Search Report of European Appln. No. 19888223.5 dated Aug. 3, 2022".

Chow, et al., "High-performance genetically targetable optical neural silencing by light-driven proton pumps", Nature, vol. 463, No. 7277, XPO55248714, Jan. 7, 2010, 98-102.

Hallett, et al., "Correlating in Vitro and in Vivo Activities of Light-Inducible Dimers: A Cellular Optogenetics Guide", ACS Synthetic Biology, vol. 5, No. 1, XP55843993, Jan. 15, 2016, 53-64.

Kennedy, et al., "Rapid blue-light mediated induction of protein interactions in living cells", Nature Methods, vol. 7, No. 12, XPO55039821,, Dec. 1, 2010, 973-975.

International Search Report and Written Opinion dated Feb. 6, 2020 for International Appln. No. PCT/US19/62620.

Park, et al., "Optogenetic protein clustering through fluorescent protein tagging and extension of CRY2", Nature Communications; 8:30, DOI: 10.1038/s41467-017-00060-2.

Pathak, et al., "Bidirectional approaches for optogenetic regulation of gene expression in mammalian cells using *Arabidopsis* cryptochrome 2", Nucleic Acids Research, vol. 45, No. 20 e167, 2017.

Taslimi, et al., "An optimized optogenetic clustering tool for probing protein interaction and function", Nature Communications, vol. 5:4925, Sep. 18, 2014, 1-9.

* cited by examiner

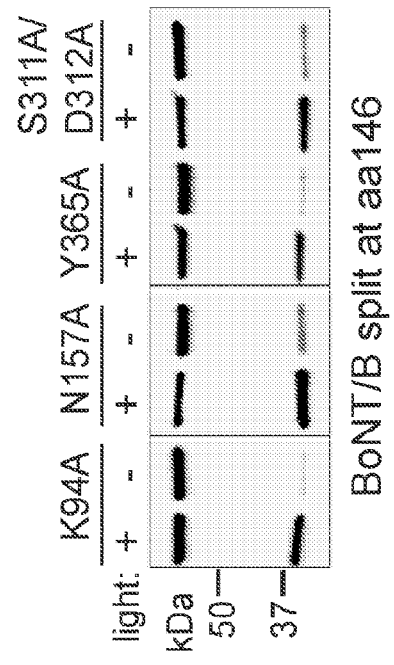
FIG. 1E
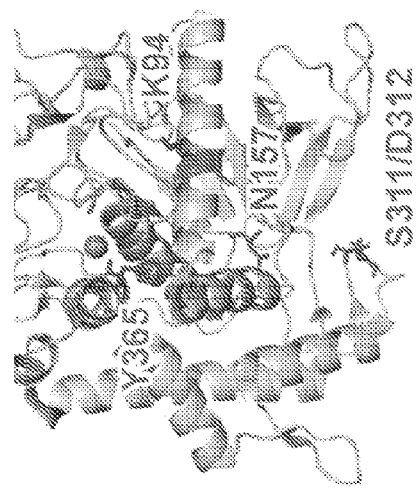
FIG. 1F
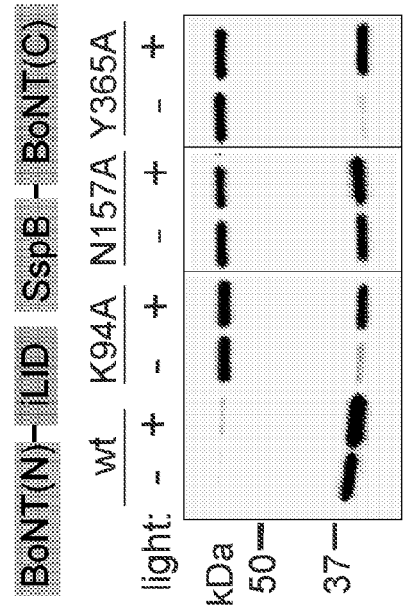
FIG. 1G
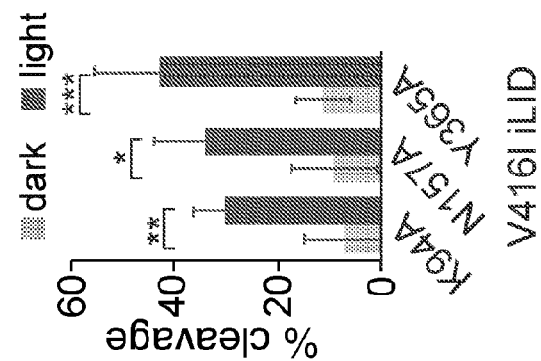
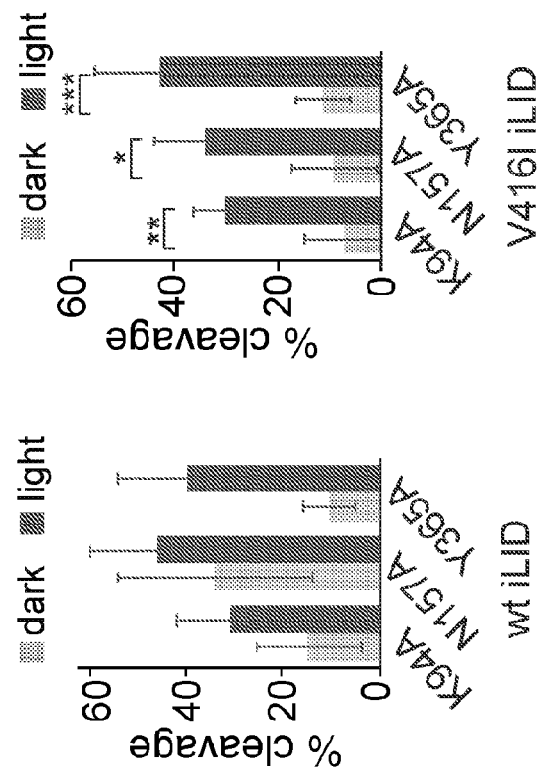
FIG. 1H

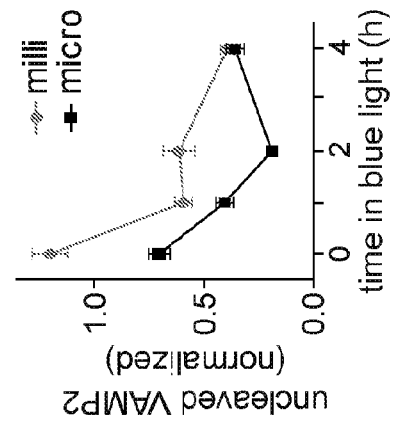
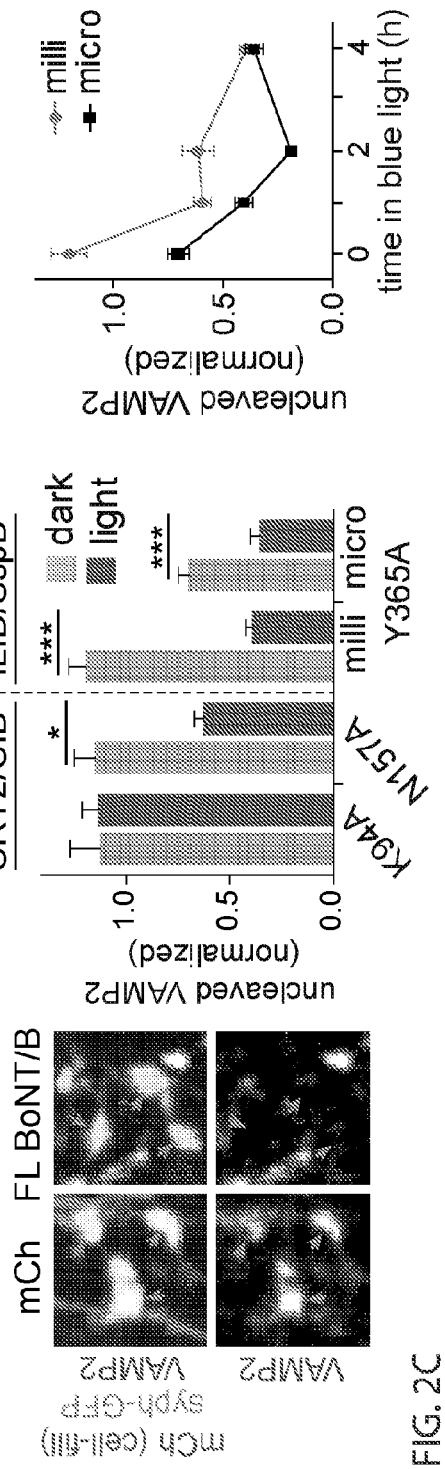
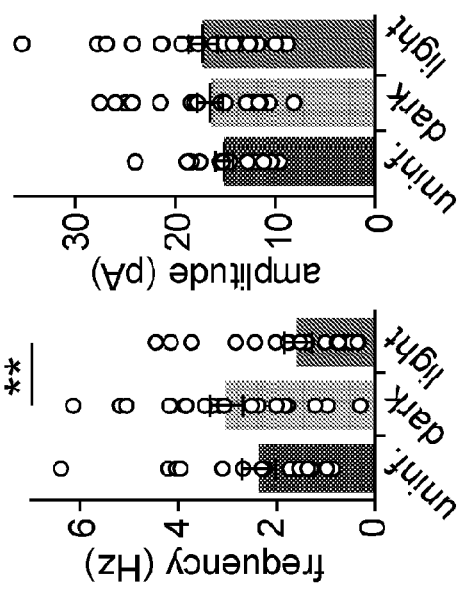
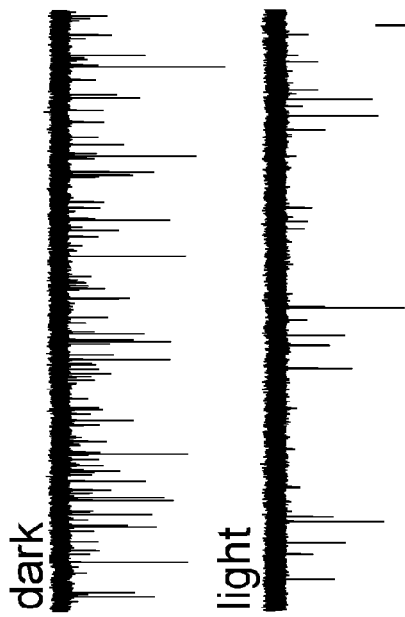
FIG. 2A
FIG. 2B
FIG. 2C

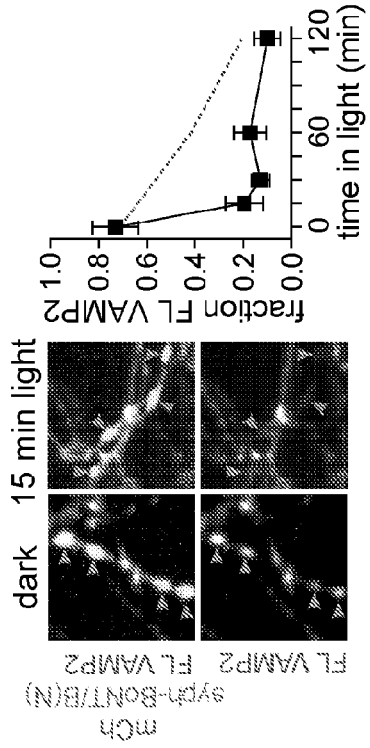
FIG. 3A
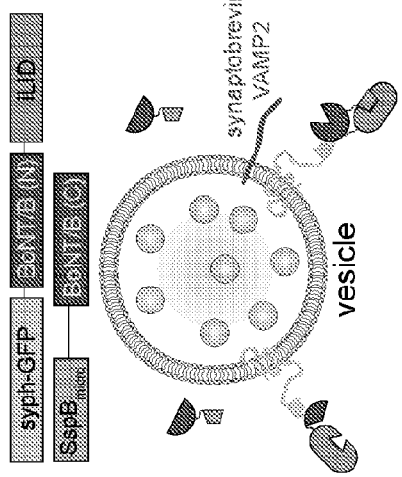
FIG. 3B
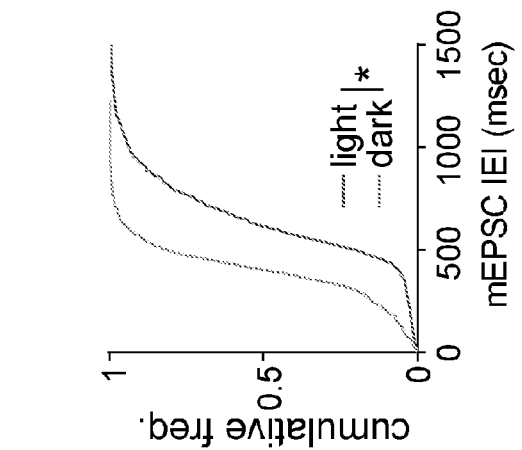
FIG. 3D
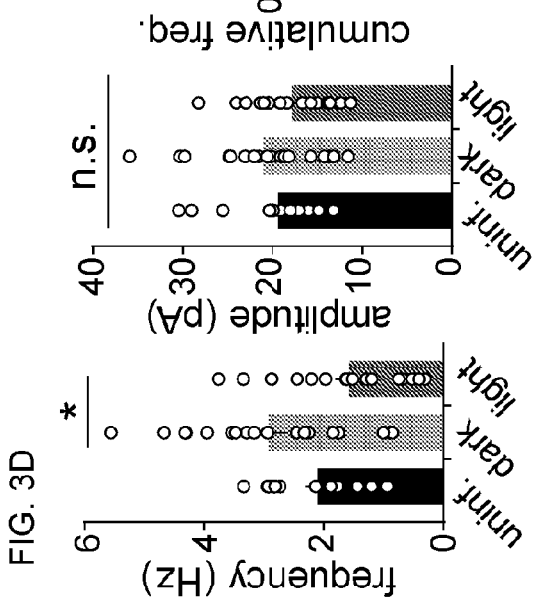
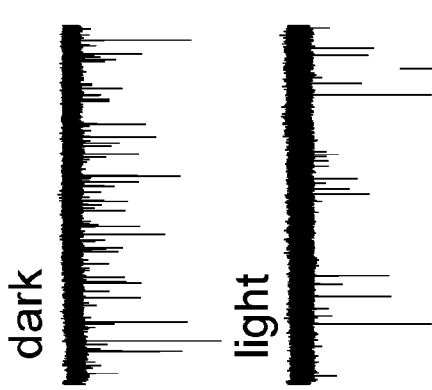
FIG. 3C

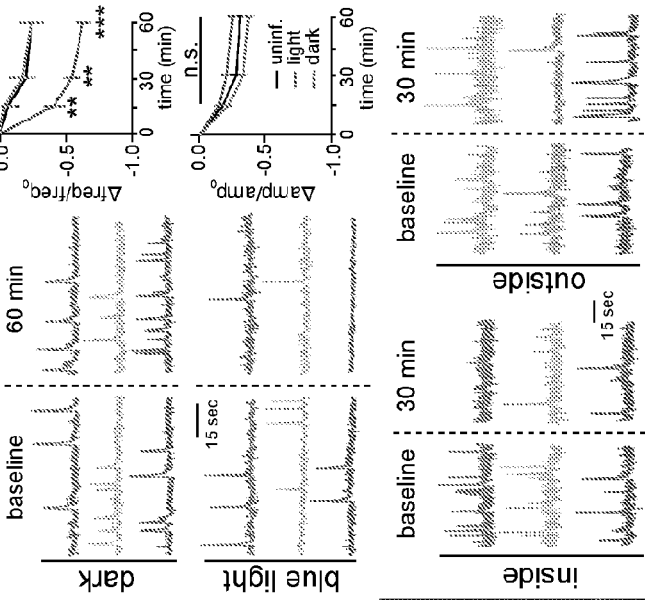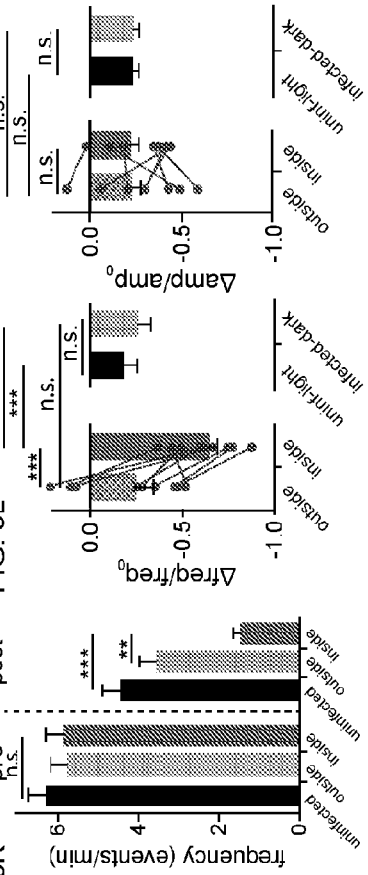

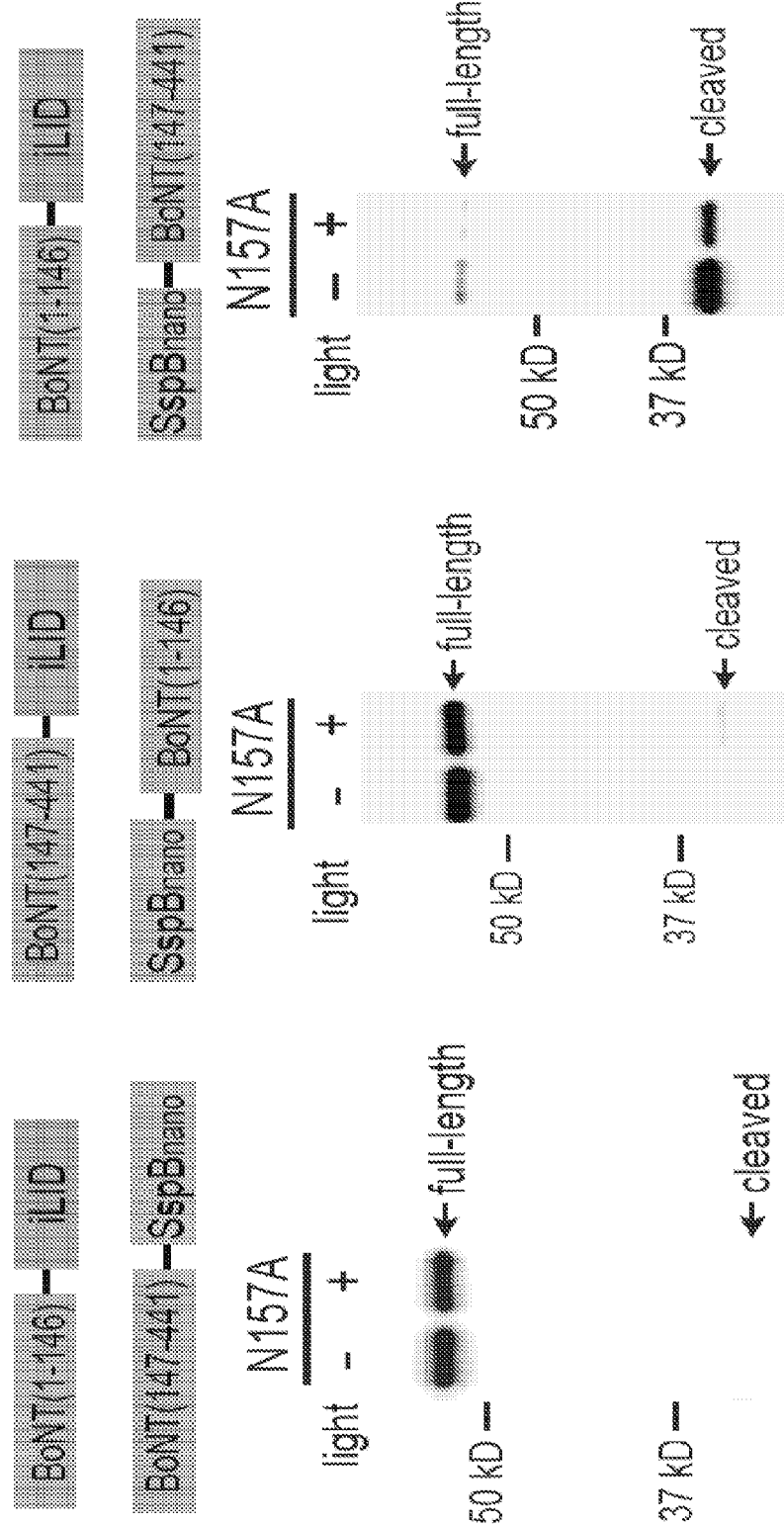

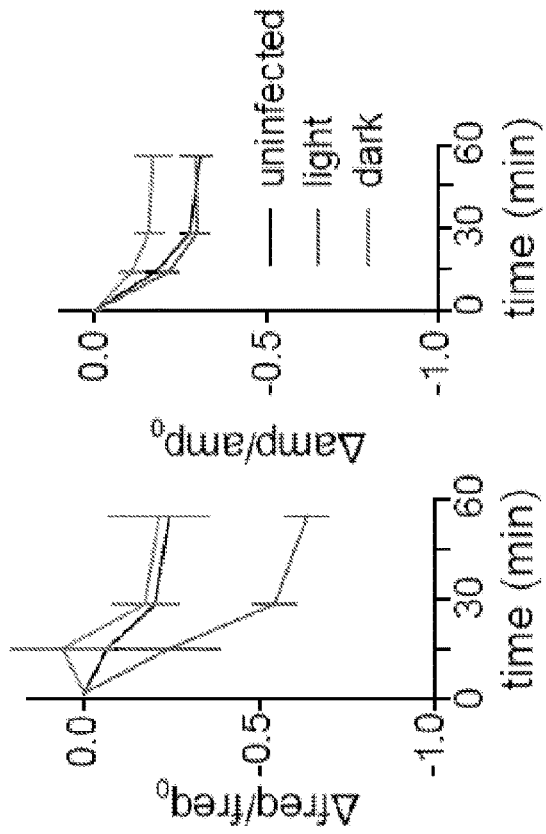
FIG. 8A
FIG. 8B
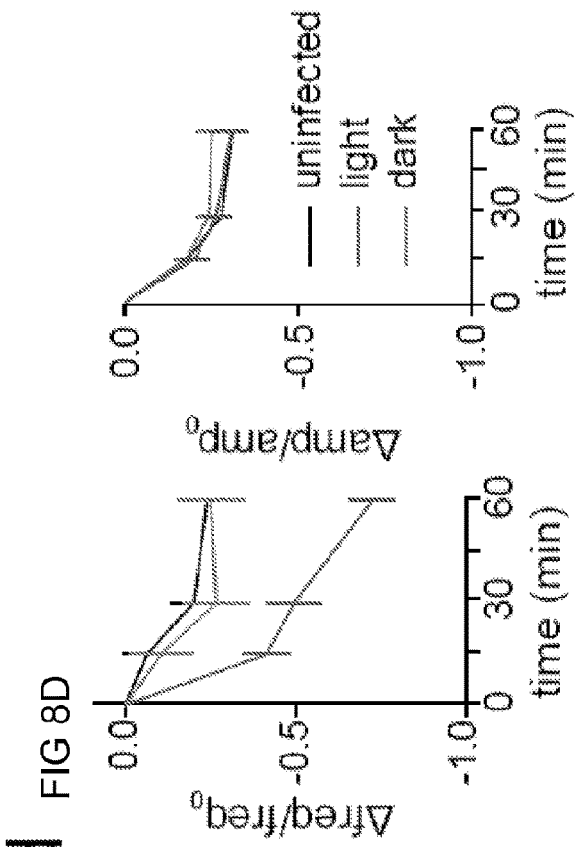
FIG. 8C
FIG. 8D

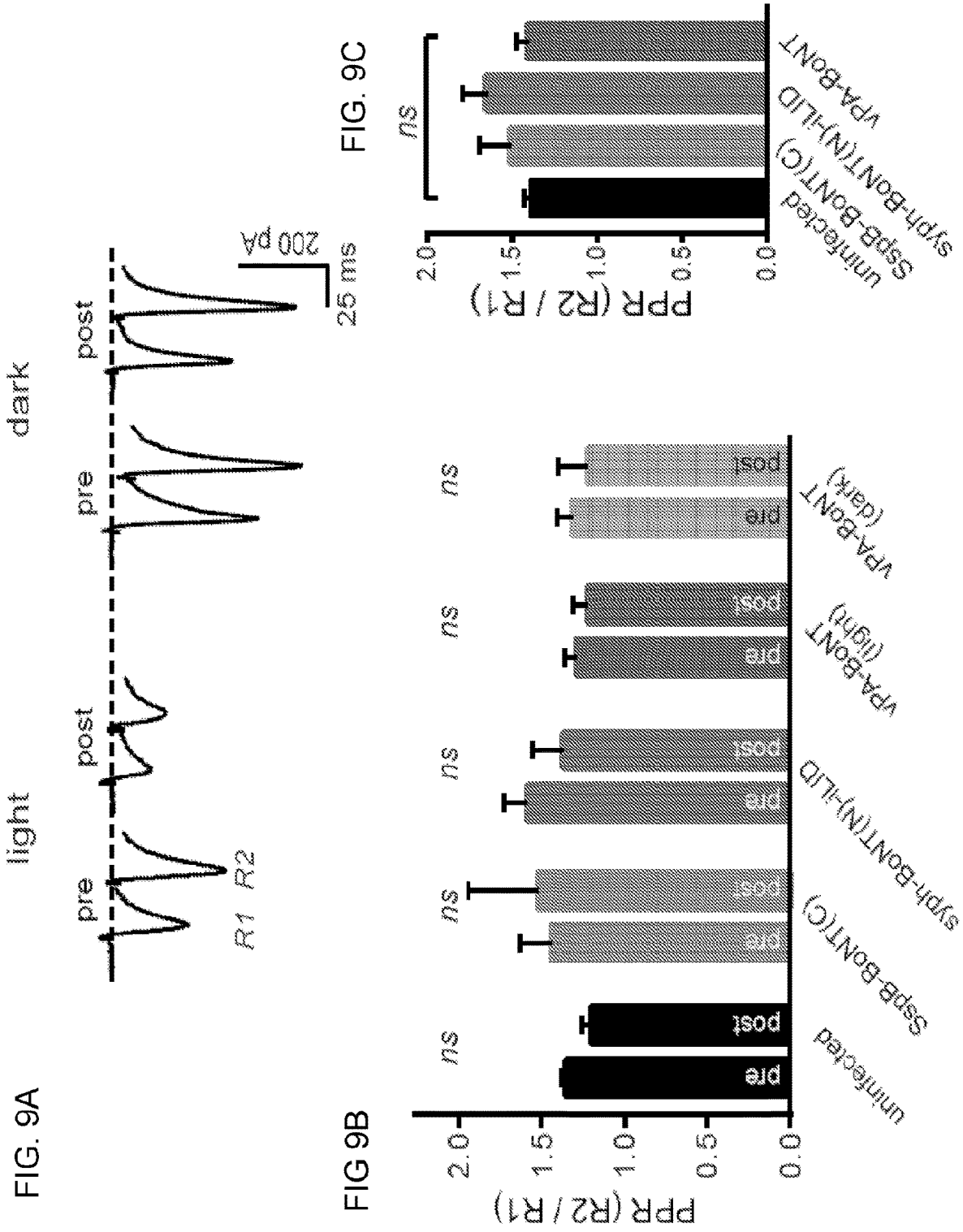

SEQUENCE LISTING

```
<160> NUMBER OF SEQ ID NOS: 46

<210> SEQ ID NO 1
<211> LENGTH: 335
<212> TYPE: PRT
<213> ORGANISM: Arabidopsis thaliana

<400> SEQUENCE: 1

Met Asn Gly Ala Ile Gly Gly Asp Leu Leu Leu Asn Phe Pro Asp Met
1               5                   10                  15

Ser Val Leu Glu Arg Gln Arg Ala His Leu Lys Tyr Leu Asn Pro Thr
            20                  25                  30

Phe Asp Ser Pro Leu Ala Gly Phe Phe Ala Asp Ser Ser Met Ile Thr
        35                  40                  45

Gly Gly Glu Met Asp Ser Tyr Leu Ser Thr Ala Gly Leu Asn Leu Pro
    50                  55                  60

Met Met Tyr Gly Glu Thr Thr Val Glu Gly Asp Ser Arg Leu Ser Ile
65                  70                  75                  80

Ser Pro Glu Thr Thr Leu Gly Thr Gly Asn Phe Lys Ala Ala Lys Phe
                85                  90                  95

Asp Thr Glu Thr Lys Asp Cys Asn Glu Ala Ala Lys Lys Met Thr Met
            100                 105                 110

Asn Arg Asp Asp Leu Val Glu Glu Gly Glu Glu Glu Lys Ser Lys Ile
```

-continued

```
                115                 120                 125
Thr Glu Gln Asn Asn Gly Ser Thr Lys Ser Ile Lys Lys Met Lys His
    130                 135                 140
Lys Ala Lys Lys Glu Glu Asn Asn Phe Ser Asn Asp Ser Ser Lys Val
145                 150                 155                 160
Thr Lys Glu Leu Glu Lys Thr Asp Tyr Ile His Val Arg Ala Arg Arg
                165                 170                 175
Gly Gln Ala Thr Asp Ser His Ser Ile Ala Glu Arg Val Arg Arg Glu
            180                 185                 190
Lys Ile Ser Glu Arg Met Lys Phe Leu Gln Asp Leu Val Pro Gly Cys
        195                 200                 205
Asp Lys Ile Thr Gly Lys Ala Gly Met Leu Asp Glu Ile Ile Asn Tyr
    210                 215                 220
Val Gln Ser Leu Gln Arg Gln Ile Glu Phe Leu Ser Met Lys Leu Ala
225                 230                 235                 240
Ile Val Asn Pro Arg Pro Asp Phe Asp Met Asp Asp Ile Phe Ala Lys
                245                 250                 255
Glu Val Ala Ser Thr Pro Met Thr Val Val Pro Ser Pro Glu Met Val
            260                 265                 270
Leu Ser Gly Tyr Ser His Glu Met Val His Ser Gly Tyr Ser Ser Glu
        275                 280                 285
Met Val Asn Ser Gly Tyr Leu His Val Asn Pro Met Gln Gln Val Asn
    290                 295                 300
Thr Ser Ser Asp Pro Leu Ser Cys Phe Asn Asn Gly Glu Ala Pro Ser
305                 310                 315                 320
Met Trp Asp Ser His Val Gln Asn Leu Tyr Gly Asn Leu Gly Val
                325                 330                 335

<210> SEQ ID NO 2
<211> LENGTH: 170
<212> TYPE: PRT
<213> ORGANISM: Artificial Sequence
<220> FEATURE:
<223> OTHER INFORMATION: CIBN(delta NLS) polypeptide

<400> SEQUENCE: 2

Met Asn Gly Ala Ile Gly Gly Asp Leu Leu Leu Asn Phe Pro Asp Met
1               5                   10                  15
Ser Val Leu Glu Arg Gln Arg Ala His Leu Lys Tyr Leu Asn Pro Thr
            20                  25                  30
Phe Asp Ser Pro Leu Ala Gly Phe Phe Ala Asp Ser Ser Met Ile Thr
        35                  40                  45
Gly Gly Glu Met Asp Ser Tyr Leu Ser Thr Ala Gly Leu Asn Leu Pro
    50                  55                  60
Met Met Tyr Gly Glu Thr Thr Val Glu Gly Asp Ser Arg Leu Ser Ile
65                  70                  75                  80
Ser Pro Glu Thr Thr Leu Gly Thr Gly Asn Phe Lys Ala Ala Lys Phe
                85                  90                  95
Asp Thr Glu Thr Lys Asp Cys Asn Glu Ala Ala Lys Lys Met Thr Met
            100                 105                 110
Asn Arg Asp Asp Leu Val Glu Gly Glu Glu Glu Lys Ser Lys Ile
        115                 120                 125
Thr Glu Gln Asn Asn Gly Ser Thr Lys Ser Ile Lys Lys Met Lys His
    130                 135                 140
Lys Ala Lys Lys Glu Glu Asn Asn Phe Ser Asn Asp Ser Ser Lys Val
```

```
                145                 150                 155                 160
Thr Lys Glu Leu Glu Lys Thr Asp Tyr Ile
                165                 170

<210> SEQ ID NO 3
<211> LENGTH: 612
<212> TYPE: PRT
<213> ORGANISM: Arabidopsis thaliana

<400> SEQUENCE: 3

Met Lys Met Asp Lys Lys Thr Ile Val Trp Phe Arg Arg Asp Leu Arg
1               5                   10                  15

Ile Glu Asp Asn Pro Ala Leu Ala Ala Ala His Glu Gly Ser Val
                20                  25                  30

Phe Pro Val Phe Ile Trp Cys Pro Glu Glu Gly Gln Phe Tyr Pro
                35                  40                  45

Gly Arg Ala Ser Arg Trp Trp Met Lys Gln Ser Leu Ala His Leu Ser
50                  55                  60

Gln Ser Leu Lys Ala Leu Gly Ser Asp Leu Thr Ile Lys Thr His
65                  70                  75                  80

Asn Thr Ile Ser Ala Ile Leu Asp Cys Ile Arg Val Thr Gly Ala Thr
                85                  90                  95

Lys Val Val Phe Asn His Leu Tyr Asp Pro Val Ser Leu Val Arg Asp
                100                 105                 110

His Thr Val Lys Glu Lys Leu Val Glu Arg Gly Ile Ser Val Gln Ser
                115                 120                 125

Tyr Asn Gly Asp Leu Leu Tyr Glu Pro Trp Glu Ile Tyr Cys Glu Lys
                130                 135                 140

Gly Lys Pro Phe Thr Ser Phe Asn Ser Tyr Trp Lys Lys Cys Leu Asp
145                 150                 155                 160

Met Ser Ile Glu Ser Val Met Leu Pro Pro Trp Arg Leu Met Pro
                165                 170                 175

Ile Thr Ala Ala Ala Glu Ala Ile Trp Ala Cys Ser Ile Glu Glu Leu
                180                 185                 190

Gly Leu Glu Asn Glu Ala Glu Lys Pro Ser Asn Ala Leu Leu Thr Arg
                195                 200                 205

Ala Trp Ser Pro Gly Trp Ser Asn Ala Asp Lys Leu Leu Asn Glu Phe
210                 215                 220

Ile Glu Lys Gln Leu Ile Asp Tyr Ala Lys Asn Ser Lys Lys Val Val
225                 230                 235                 240

Gly Asn Ser Thr Ser Leu Leu Ser Pro Tyr Leu His Phe Gly Glu Ile
                245                 250                 255

Ser Val Arg His Val Phe Gln Cys Ala Arg Met Lys Gln Ile Ile Trp
                260                 265                 270

Ala Arg Asp Lys Asn Ser Glu Gly Glu Glu Ser Ala Asp Leu Phe Leu
                275                 280                 285

Arg Gly Ile Gly Leu Arg Glu Tyr Ser Arg Tyr Ile Cys Phe Asn Phe
                290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
                340                 345                 350
```

Trp Met His Asn Arg Ile Arg Val Ile Val Ser Ser Phe Ala Val Lys
            355                 360                 365

Phe Leu Leu Leu Pro Trp Lys Trp Gly Met Lys Tyr Phe Trp Asp Thr
        370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Gly Glu Tyr Ile Arg Gln
            420                 425                 430

Trp Leu Pro Glu Leu Ala Arg Leu Pro Thr Glu Trp Ile His His Pro
        435                 440                 445

Trp Asp Ala Pro Leu Thr Val Leu Lys Ala Ser Gly Val Glu Leu Gly
    450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
            485                 490                 495

Ala Ala Pro Asp Glu Ile Val Ala Asp Ser Phe Glu Ala Leu Gly Ala
        500                 505                 510

Asn Thr Ile Lys Glu Pro Gly Leu Cys Pro Ser Val Ser Ser Asn Asp
    515                 520                 525

Gln Gln Val Pro Ser Ala Val Arg Tyr Asn Gly Ser Ala Ala Val Lys
            530                 535                 540

Pro Glu Glu Glu Glu Arg Asp Met Lys Lys Ser Arg Gly Phe Asp
545                 550                 555                 560

Glu Arg Glu Leu Phe Ser Thr Ala Glu Ser Ser Ser Ser Ser Ser Val
            565                 570                 575

Phe Phe Val Ser Gln Ser Cys Ser Leu Ala Ser Glu Gly Lys Asn Leu
        580                 585                 590

Glu Gly Ile Gln Asp Ser Ser Asp Gln Ile Thr Thr Ser Leu Gly Lys
            595                 600                 605

Asn Gly Cys Lys
        610

<210> SEQ ID NO 4
<211> LENGTH: 441
<212> TYPE: PRT
<213> ORGANISM: Clostridium botulinum

<400> SEQUENCE: 4

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

```
Ile Asn Gly Ile Pro Tyr Leu Gly Asp Arg Arg Val Pro Leu Glu Glu
            115                 120                 125

Phe Asn Thr Asn Ile Ala Ser Val Thr Val Asn Lys Leu Ile Ser Asn
        130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys
        435                 440

<210> SEQ ID NO 5
<211> LENGTH: 148
<212> TYPE: PRT
<213> ORGANISM: Artificial Sequence
<220> FEATURE:
<223> OTHER INFORMATION: LOV domain-peptide fusion (iLID)

<400> SEQUENCE: 5

Glu Phe Leu Ala Thr Thr Leu Glu Arg Ile Glu Lys Asn Phe Val Ile
1               5                   10                  15

Thr Asp Pro Arg Leu Pro Asp Asn Pro Ile Ile Phe Ala Ser Asp Ser
            20                  25                  30
```

```
Phe Leu Gln Leu Thr Glu Tyr Ser Arg Glu Ile Leu Gly Arg Asn
                35                  40                  45

Cys Arg Phe Leu Gln Gly Pro Glu Thr Asp Arg Ala Thr Val Arg Lys
 50                  55                  60

Ile Arg Asp Ala Ile Asp Asn Gln Thr Glu Val Thr Val Gln Leu Ile
 65                  70                  75                  80

Asn Tyr Thr Lys Ser Gly Lys Lys Phe Trp Asn Val Phe His Leu Gln
                 85                  90                  95

Pro Met Arg Asp Tyr Lys Gly Asp Val Gln Tyr Phe Ile Gly Val Gln
                100                 105                 110

Leu Asp Gly Thr Glu Arg Leu His Gly Ala Ala Glu Arg Glu Ala Val
                115                 120                 125

Cys Leu Ile Lys Lys Thr Ala Phe Gln Ile Ala Glu Ala Ala Asn Asp
130                 135                 140

Glu Asn Tyr Phe
145

<210> SEQ ID NO 6
<211> LENGTH: 113
<212> TYPE: PRT
<213> ORGANISM: E. coli

<400> SEQUENCE: 6

Glu Phe Ser Ser Pro Lys Arg Pro Lys Leu Leu Arg Glu Tyr Tyr Asp
 1                   5                  10                  15

Trp Leu Val Asp Asn Ser Phe Thr Pro Tyr Leu Val Val Asp Ala Thr
                 20                  25                  30

Tyr Leu Gly Val Asn Val Pro Val Glu Tyr Val Lys Asp Gly Gln Ile
                 35                  40                  45

Val Leu Asn Leu Ser Ala Ser Ala Thr Gly Asn Leu Gln Leu Thr Asn
 50                  55                  60

Asp Phe Ile Gln Phe Asn Ala Arg Phe Lys Gly Val Ser Arg Glu Leu
 65                  70                  75                  80

Tyr Ile Pro Met Gly Ala Ala Leu Ala Ile Tyr Ala Arg Glu Asn Gly
                 85                  90                  95

Asp Gly Val Met Phe Glu Pro Glu Glu Ile Tyr Asp Glu Leu Asn Ile
                100                 105                 110

Gly

<210> SEQ ID NO 7
<211> LENGTH: 113
<212> TYPE: PRT
<213> ORGANISM: E. coli

<400> SEQUENCE: 7

Glu Phe Ser Ser Pro Lys Arg Pro Lys Leu Leu Arg Glu Tyr Tyr Asp
 1                   5                  10                  15

Trp Leu Val Asp Asn Ser Phe Thr Pro Tyr Leu Val Val Asp Ala Thr
                 20                  25                  30

Tyr Leu Gly Val Asn Val Pro Val Glu Tyr Val Lys Asp Gly Gln Ile
                 35                  40                  45

Val Leu Asn Leu Ser Ala Ser Val Thr Gly Asn Leu Gln Leu Thr Asn
 50                  55                  60

Asp Phe Ile Gln Phe Asn Ala Gln Phe Lys Gly Val Ser Arg Glu Leu
 65                  70                  75                  80
```

```
Tyr Ile Pro Met Gly Ala Ala Leu Ala Ile Tyr Ala Arg Glu Asn Gly
                85                  90                  95

Asp Gly Val Met Phe Glu Pro Glu Ile Tyr Asp Glu Leu Asn Ile
            100                 105                 110

Gly

<210> SEQ ID NO 8
<211> LENGTH: 113
<212> TYPE: PRT
<213> ORGANISM: E. coli

<400> SEQUENCE: 8

Glu Phe Ser Ser Pro Lys Arg Pro Lys Leu Leu Arg Glu Tyr Tyr Asp
1               5                   10                  15

Trp Leu Val Asp Asn Ser Phe Thr Pro Tyr Leu Val Val Asp Ala Thr
            20                  25                  30

Tyr Leu Gly Val Asn Val Pro Val Glu Tyr Val Lys Asp Gly Gln Ile
            35                  40                  45

Val Leu Asn Leu Ser Ala Ser Ala Thr Gly Asn Leu Gln Leu Thr Asn
50                  55                  60

Asp Phe Ile Gln Phe Asn Ala Gln Phe Lys Gly Val Ser Arg Glu Leu
65                  70                  75                  80

Tyr Ile Pro Met Gly Ala Ala Leu Ala Ile Tyr Ala Arg Glu Asn Gly
                85                  90                  95

Asp Gly Val Met Phe Glu Pro Glu Ile Tyr Asp Glu Leu Asn Ile
            100                 105                 110

Gly

<210> SEQ ID NO 9
<211> LENGTH: 448
<212> TYPE: PRT
<213> ORGANISM: Clostridium botulinum

<400> SEQUENCE: 9

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
            35                  40                  45

Asp Thr Phe Thr Asn Pro Glu Glu Gly Asp Leu Asn Pro Pro Pro Glu
50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175
```

-continued

```
Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445
```

<210> SEQ ID NO 10
<211> LENGTH: 58
<212> TYPE: DNA
<213> ORGANISM: Artificial Sequence
<220> FEATURE:
<223> OTHER INFORMATION: Oligo

<400> SEQUENCE: 10
ggacccacca cctccagagc caccgccacc atgaatataa tccgtttctt ccaattcc    58

<210> SEQ ID NO 11
<211> LENGTH: 72
<212> TYPE: DNA
<213> ORGANISM: Artificial Sequence
<220> FEATURE:
<223> OTHER INFORMATION: Oligo

<400> SEQUENCE: 11
tcaactccaa gctggccgct ctagaactag tgagctcgcc accatgaaga tggacaaaaa    60
gactatagtt tg                                                        72

```
<210> SEQ ID NO 12
<211> LENGTH: 66
<212> TYPE: DNA
<213> ORGANISM: Artificial Sequence
<220> FEATURE:
<223> OTHER INFORMATION: Oligo

<400> SEQUENCE: 12
tcaactccaa gctggccgct ctagaactag tgagctcgcc accatgaatg gagctatagg      60
aggtga                                                                66

<210> SEQ ID NO 13
<211> LENGTH: 41
<212> TYPE: DNA
<213> ORGANISM: Artificial Sequence
<220> FEATURE:
<223> OTHER INFORMATION: Oligo

<400> SEQUENCE: 13
ttaagcggcc gcctcctccg gacccaccac ctccagagcc a                          41

<210> SEQ ID NO 14
<211> LENGTH: 60
<212> TYPE: DNA
<213> ORGANISM: Artificial Sequence
<220> FEATURE:
<223> OTHER INFORMATION: Oligo

<400> SEQUENCE: 14
ttaaggatcc gcggccgcat gccagttaca ataaataatt ttaattataa tgatcctatt      60

<210> SEQ ID NO 15
<211> LENGTH: 55
<212> TYPE: DNA
<213> ORGANISM: Artificial Sequence
<220> FEATURE:
<223> OTHER INFORMATION: Oligo

<400> SEQUENCE: 15
ttaagaattc ccgggctatt taacactttt acacatttgt atcttatata cagcc            55

<210> SEQ ID NO 16
<211> LENGTH: 55
<212> TYPE: DNA
<213> ORGANISM: Artificial Sequence
<220> FEATURE:
<223> OTHER INFORMATION: Oligo

<400> SEQUENCE: 16
ttaagcggcc gcactaatga taaaagaat atattttac aaacaatgat caagt             55

<210> SEQ ID NO 17
<211> LENGTH: 50
<212> TYPE: DNA
<213> ORGANISM: Artificial Sequence
<220> FEATURE:
<223> OTHER INFORMATION: Oligo

<400> SEQUENCE: 17
ttaacccggg tcaatttaag taatctggat cataatattc acaaacatct                 50

<210> SEQ ID NO 18
<211> LENGTH: 44
<212> TYPE: DNA
<213> ORGANISM: Artificial Sequence
<220> FEATURE:
```

<223> OTHER INFORMATION: Oligo

<400> SEQUENCE: 18
ttaagcggcc gcgcaagtat atttaataga cgtggatatt tttc					44

<210> SEQ ID NO 19
<211> LENGTH: 45
<212> TYPE: DNA
<213> ORGANISM: Artificial Sequence
<220> FEATURE:
<223> OTHER INFORMATION: Oligo

<400> SEQUENCE: 19
ttaacccggg tcagcctttg ttttcttgaa cattattaaa tacgc					45

<210> SEQ ID NO 20
<211> LENGTH: 40
<212> TYPE: DNA
<213> ORGANISM: Artificial Sequence
<220> FEATURE:
<223> OTHER INFORMATION: Oligo

<400> SEQUENCE: 20
ttaagcggcc gcgaagtgga gcgaaaaaaa ggtattttcg					40

<210> SEQ ID NO 21
<211> LENGTH: 48
<212> TYPE: DNA
<213> ORGANISM: Artificial Sequence
<220> FEATURE:
<223> OTHER INFORMATION: Oligo

<400> SEQUENCE: 21
ttaacccggg tcatcctgga ttactgatta atttattaac agttacac					48

<210> SEQ ID NO 22
<211> LENGTH: 46
<212> TYPE: DNA
<213> ORGANISM: Artificial Sequence
<220> FEATURE:
<223> OTHER INFORMATION: Oligo

<400> SEQUENCE: 22
ttaagcggcc gcaaattttt tatgcaatct acagatgcta tacagg					46

<210> SEQ ID NO 23
<211> LENGTH: 47
<212> TYPE: DNA
<213> ORGANISM: Artificial Sequence
<220> FEATURE:
<223> OTHER INFORMATION: Oligo

<400> SEQUENCE: 23
ttaacccggg tcatttttca tttggtacaa ttggtaaatc atctact					47

<210> SEQ ID NO 24
<211> LENGTH: 58
<212> TYPE: DNA
<213> ORGANISM: Artificial Sequence
<220> FEATURE:
<223> OTHER INFORMATION: Oligo

<400> SEQUENCE: 24
ttaagagctc gccaccatgc cagttacaat aaataatttt aattataatg atcctatt					58

```
<210> SEQ ID NO 25
<211> LENGTH: 18
<212> TYPE: DNA
<213> ORGANISM: Artificial Sequence
<220> FEATURE:
<223> OTHER INFORMATION: Oligo

<400> SEQUENCE: 25
ttaaaccggt cgccacca                                                    18

<210> SEQ ID NO 26
<211> LENGTH: 56
<212> TYPE: DNA
<213> ORGANISM: Artificial Sequence
<220> FEATURE:
<223> OTHER INFORMATION: Oligo

<400> SEQUENCE: 26
ttaagcggcc gcctcctcct gaacctccac ccgcggaaga gacaacccac acgatg          56

<210> SEQ ID NO 27
<211> LENGTH: 41
<212> TYPE: DNA
<213> ORGANISM: Artificial Sequence
<220> FEATURE:
<223> OTHER INFORMATION: Oligo

<400> SEQUENCE: 27
ttaagcggcc gcatgaccaa gttacctata ctaggttatt g                          41

<210> SEQ ID NO 28
<211> LENGTH: 34
<212> TYPE: DNA
<213> ORGANISM: Artificial Sequence
<220> FEATURE:
<223> OTHER INFORMATION: Oligo

<400> SEQUENCE: 28
ttaatctaga ctcaaaccag atgatccgat tttg                                  34

<210> SEQ ID NO 29
<211> LENGTH: 54
<212> TYPE: DNA
<213> ORGANISM: Artificial Sequence
<220> FEATURE:
<223> OTHER INFORMATION: Oligo

<400> SEQUENCE: 29
ttaactcgag ccaccatgcc agttacaata ataattttta attataatga tcct            54

<210> SEQ ID NO 30
<211> LENGTH: 48
<212> TYPE: DNA
<213> ORGANISM: Artificial Sequence
<220> FEATURE:
<223> OTHER INFORMATION: Oligo

<400> SEQUENCE: 30
ttaagcggcc gcctcctgga ttactgatta atttattaac agttacac                   48

<210> SEQ ID NO 31
<211> LENGTH: 50
<212> TYPE: DNA
<213> ORGANISM: Artificial Sequence
<220> FEATURE:
<223> OTHER INFORMATION: Oligo
```

<400> SEQUENCE: 31
gtggcggtgg ctctggaggt gggtccgagc tcggggagtt tctggcaacc            50

<210> SEQ ID NO 32
<211> LENGTH: 32
<212> TYPE: DNA
<213> ORGANISM: Artificial Sequence
<220> FEATURE:
<223> OTHER INFORMATION: Oligo

<400> SEQUENCE: 32
ttaagcggcc gcagcggtgg cggtggctct gg                               32

<210> SEQ ID NO 33
<211> LENGTH: 43
<212> TYPE: DNA
<213> ORGANISM: Artificial Sequence
<220> FEATURE:
<223> OTHER INFORMATION: Oligo

<400> SEQUENCE: 33
ttaacccggg cttaagtcaa aagtaattttt cgtcgttcgc tgc                  43

<210> SEQ ID NO 34
<211> LENGTH: 46
<212> TYPE: DNA
<213> ORGANISM: Artificial Sequence
<220> FEATURE:
<223> OTHER INFORMATION: Oligo

<400> SEQUENCE: 34
ttaactcgag ccaccatgga agtggagcga aaaaaggta ttttcg                 46

<210> SEQ ID NO 35
<211> LENGTH: 56
<212> TYPE: DNA
<213> ORGANISM: Artificial Sequence
<220> FEATURE:
<223> OTHER INFORMATION: Oligo

<400> SEQUENCE: 35
ttaatccgga gccgccacct ttaacactttt tacacatttg tatcttatat acagcc    56

<210> SEQ ID NO 36
<211> LENGTH: 55
<212> TYPE: DNA
<213> ORGANISM: Artificial Sequence
<220> FEATURE:
<223> OTHER INFORMATION: Oligo

<400> SEQUENCE: 36
ttaatccgga ggcggtggct ctggaggtgg gtccgaattc agctccccga aacgc      55

<210> SEQ ID NO 37
<211> LENGTH: 46
<212> TYPE: DNA
<213> ORGANISM: Artificial Sequence
<220> FEATURE:
<223> OTHER INFORMATION: Oligo

<400> SEQUENCE: 37
ttaacccggg atatctcaac caatattcag ctcgtcatag atttct                46

<210> SEQ ID NO 38
<211> LENGTH: 29

<212> TYPE: DNA
<213> ORGANISM: Artificial Sequence
<220> FEATURE:
<223> OTHER INFORMATION: Oligo

<400> SEQUENCE: 38
ttaagaattc ctggcaacca cactggaac                                    29

<210> SEQ ID NO 39
<211> LENGTH: 40
<212> TYPE: DNA
<213> ORGANISM: Artificial Sequence
<220> FEATURE:
<223> OTHER INFORMATION: Oligo

<400> SEQUENCE: 39
ttaactcgag gccaccatgg aatacagctc cccgaaacgc                        40

<210> SEQ ID NO 40
<211> LENGTH: 60
<212> TYPE: DNA
<213> ORGANISM: Artificial Sequence
<220> FEATURE:
<223> OTHER INFORMATION: Oligo

<400> SEQUENCE: 40
caccacctcc agagccaccg ccaccgagct caatattcag ctcgtcatag atttcttctg  60

<210> SEQ ID NO 41
<211> LENGTH: 40
<212> TYPE: DNA
<213> ORGANISM: Artificial Sequence
<220> FEATURE:
<223> OTHER INFORMATION: Oligo

<400> SEQUENCE: 41
ttaaagatct gctagcgcca ccatggtgag caagggcgag                        40

<210> SEQ ID NO 42
<211> LENGTH: 49
<212> TYPE: DNA
<213> ORGANISM: Artificial Sequence
<220> FEATURE:
<223> OTHER INFORMATION: Oligo

<400> SEQUENCE: 42
ttaagaattc atttaacact tttacacatt tgtatcttat atacagcca              49

<210> SEQ ID NO 43
<211> LENGTH: 36
<212> TYPE: DNA
<213> ORGANISM: Artificial Sequence
<220> FEATURE:
<223> OTHER INFORMATION: Oligo

<400> SEQUENCE: 43
ttaagaattc aaaagtaatt ttcgtcgttc gctgcc                            36

<210> SEQ ID NO 44
<211> LENGTH: 37
<212> TYPE: DNA
<213> ORGANISM: Artificial Sequence
<220> FEATURE:
<223> OTHER INFORMATION: Oligo

<400> SEQUENCE: 44

```
ttaagctagc gccaccatgg acgtggtgaa tcagctg                          37

<210> SEQ ID NO 45
<211> LENGTH: 58
<212> TYPE: DNA
<213> ORGANISM: Artificial Sequence
<220> FEATURE:
<223> OTHER INFORMATION: Oligo

<400> SEQUENCE: 45
ttaagtcgac agcgtaatct ggaacatcgt atgggtactt gtacagctcg tccatgcc   58

<210> SEQ ID NO 46
<211> LENGTH: 60
<212> TYPE: DNA
<213> ORGANISM: Artificial Sequence
<220> FEATURE:
<223> OTHER INFORMATION: Oligo

<400> SEQUENCE: 46
ttagtcgacc cagatcctct tctgagatga gtttttgttc cttgtacagc tcgtccatgc 60
```

PROTEINS FOR BLOCKING NEUROTRANSMITTER RELEASE

CROSS-REFERENCE TO RELATED APPLICATIONS

The present application is a 35 U.S.C. § 371 national phase application from, and claims priority to, PCT International Patent Application No. PCT/US2019/062620, filed Nov. 21, 2019, which claims priority under 35 U.S.C. § 119 (e) to U.S. Provisional Application No. 62/770,520, filed Nov. 21, 2018, all of which are incorporated herein by reference in their entireties.

STATEMENT REGARDING FEDERALLY SPONSORED RESEARCH OR DEVELOPMENT

This invention was made with government support under EY026363 and 1UF1NS107710 awarded by the National Institutes of Health. The government has certain rights in the invention.

BACKGROUND OF THE INVENTION

Much interest exists in the development of protein-based systems that allow for controlled, rapid, and localized activation of proteins. Such technology should allow for reduced systemic exposure to such activated proteins, as well as allow for localized manipulation of biological functions. For example, tools for rapidly and locally silencing distinct populations of neurons have been indispensable for assigning circuit function to in vivo behaviors. Microbial ion pumps (e.g. halorhodopsin or archaerhodopsin), which hyperpolarize neurons during illumination, allow for neural silencing on millisecond to second timescales. However, many experiments require longer term (minutes to hours) silencing that can be difficult to achieve with the current optogenetic toolkit. Most opsin-based silencing strategies require continuous illumination, making photodamage and tissue heating a concern for long-term silencing. Moreover, persistent activation of widely used chloride pump-based opsins leads to buildup of intracellular chloride to levels where activation of GABAa receptors can cause depolarization rather than hyperpolarization. Complementary chemogenetic approaches for longer-term neuronal silencing have been developed, including ivermectin-gated chloride channels, allatostatin-activated receptors, designer receptors exclusively activated by designer drugs (DREADDs), and engineered inhibitory neurotransmitter receptors, but these approaches lack the fine spatial and temporal control of optogenetics.

A classic experimental approach for long-term disruption of synaptic transmission is through genetic expression or direct application of *Clostridium botulinum* or *tetanus* neurotoxin. The catalytic light chains of these toxins are zinc-dependent endoproteases that cleave conserved soluble N-ethylmaleimide-sensitive factor attachment protein receptor (SNARE) family proteins that are critical for vesicle docking and fusion with the plasma membrane. While some degree of temporal control can be achieved using inducible expression of these toxins via regulated promoter or recombinase systems, rapid and local control is not currently possible.

There is a need in the art for novel compositions and methods that allow for controlled, rapid and localized blocking of neuronal activity. In certain embodiments, such compositions should be biologically orthogonal and combine the sustained silencing qualities of chemogenetic approaches with the spatial control of optogenetics. The present invention satisfies this need.

SUMMARY OF THE INVENTION

In one aspect, the invention provides a light-controlled protein system including: a first construct comprising a first fragment of the protein, wherein the first fragment is fused to a first photodimerizer molecule; a second construct comprising a second fragment of the protein, wherein the second fragment is fused to a second photodimerizer molecule; wherein, in the absence of visible light, the first photodimerizer molecule does not bind to the second photodimerizer molecule, forming a non-activated system; wherein, in the presence of visible light, the first photodimerizer molecule binds to the second photodimerizer molecule, thus promoting physical contact between the first fragment of the protein and the second fragment of the protein, and forming an activated system; wherein the biological activity of the protein in the activated system is higher than in the non-activated system.

In another aspect, the invention comprises a composition comprising a first adeno-associated viral (AAV) vector comprising a nucleotide sequence encoding the amino acid sequence of the first construct of the invention, and a second AAV vector comprising a nucleotide sequence encoding the amino acid sequence of the second construct of the invention, wherein the first and second vectors are the same or distinct.

In yet another aspect, the invention provides a method of locally silencing a neuron, the method comprising administering to a subject the composition of the invention, such that the composition contacts the neuron to be silenced, under conditions that allow for expression of the system of the invention, and applying visible light to the neuron, or its vicinity, whereby an activated system is formed in the neuron, or its vicinity.

In yet another aspect, the invention provides a composition comprising a first BoNT/B light chain fragment comprising amino acid residues 1-146 of SEQ ID NO:4 and a second BoNT/B light chain fragment comprising amino acid residues 147-441 of SEQ ID NO:4, wherein, when the first and second fragments are physically separate, a functional protein is not formed, and wherein, when the first and second fragments are physically adjacent, a functional protein is formed.

In yet another aspect, the invention provides a composition comprising a first BoNT/A light chain fragment comprising amino acid residues 1-203 of SEQ ID NO:9 and a second BoNT/A light chain fragment comprising amino acid residues 203-448 of SEQ ID NO:9, wherein, when the first and second fragments are physically separate, a functional protein is not formed, and wherein, when the first and second fragments are physically adjacent, a functional protein is formed.

In certain embodiments, the visible light is a blue light.

In certain embodiments, the protein is a *Clostridium botulinum* neurotoxin, or a biologically active fragment thereof. In certain embodiments, the *Clostridium botulinum* neurotoxin is serotype B (BoNT/B).

In certain embodiments, the first fragment of the protein comprises an N-terminal portion of the neurotoxin light chain, and wherein the second fragment of the protein comprises a C-terminal portion of the neurotoxin light chain.

In certain embodiments, the first photodimerizer molecule comprises a cryptochrome 2 (CRY2) molecule, and the second photodimerizer molecule comprises CIBN.

In certain embodiments, the first photodimerizer molecule comprises a LOV domain-peptide fusion (iLID), and the second photodimerizer molecule comprises a domain of *E. coli* SspB.

In certain embodiments, the iLID has a V416I mutation.

In certain embodiments, the SspB comprises SspB A58V/R73Q (SspBmilli).

In certain embodiments, the first fragment comprises amino acid residues 1-146 of SEQ ID NO:4, and the second fragment comprises amino acid residues 147-441 of SEQ ID NO:4. In certain embodiments, the second fragment has at least one mutation selected from the group consisting of K94A, N157A, Y365A, and S311A/D312A in the corresponding residues of SEQ ID NO:4.

In certain embodiments, a synaptic vesicle protein synaptophysin (Syph) is fused to the either the first construct or to the second construct.

In certain embodiments, the subject is a human.

BRIEF DESCRIPTION OF THE DRAWINGS

The following detailed description of specific embodiments of the invention will be better understood when read in conjunction with the appended drawings. For the purpose of illustrating the invention, exemplary embodiments are shown in the drawings. It should be understood, however, that the invention is not limited to the precise arrangements and instrumentalities of the embodiments shown in the drawings.

FIGS. 1A-1H illustrate the finding that split BoNT/B fragments can be reconstituted on their own or with photodimerizers. FIG. 1A is a schematic illustrating light-triggered reconstitution of split BoNT/B light chain N- and C-ter istry as in FIG. 3B. FIG. 3G shows that postsynaptic $Ca^{2+}$ transients arising from quantal neurotransmitter release events can be detected with jRGECO. Shown is a dendritic segment from a cultured hippocampal neuron expressing jRGECO (top). The middle panel shows jRGECO within a single dendritic spine before, at the peak and 2 sec following a $Ca^{2+}$ transient. The bottom panel is a kymograph generated from the red line in the top panel. Two discrete events (arrowheads) can be observed in this example. FIG. 3H shows representative traces showing spontaneous $Ca^{2+}$ transients at the same synapses before (left, baseline) and 60 min following (right) continuous darkness (top traces) or blue light exposure (bottom traces). FIG. 3I shows quantification of the frequency (top) and amplitude (bottom) of spontaneous $Ca^{2+}$ transients monitored at the same synapses over time following onset of light exposure at t=0. Data for each synapse was subtracted from its baseline (pre-light exposure) value and then divided by its baseline value. Cultures infected with vPA-BoNT (blue) show significantly reduced frequency, but not amplitude of spontaneous $Ca^{2+}$ transients within minutes compared to uninfected control neurons treated with light (black) or vPA-BoNT expressing cultures not exposed to blue light (grey). FIG. 3J shows local activation of vPA-BoNT. Cultures infected with vPA-BoNT were locally photoactivated using uniform illumination from a digital micromirror array (white box, dashed line). Representative traces to the right show $Ca^{2+}$ signals from the synapses (outlined by colored squares corresponding to colored traces) either inside (left) or outside (right) of the illuminated region. FIG. 3K shows quantification of the absolute frequency of spontaneous synaptic $Ca^{2+}$ transients in uninfected, light-treated cultures (black) and infected cultures, with synapses quantified from the same cells either "outside" (grey) or "inside" (blue) the illuminated region. The bars to the left of the dashed line display baseline event frequency at individual synapses while bars to the right of the dashed line display event frequency 30 min following local illumination. FIG. 3L shows normalized data comparing the frequency (left) and amplitude (right) of $Ca^{2+}$ transients at the same synapses before and 30 min following local illumination. The line pairings represent synapses from the same neuron that were either "inside" (blue) or "outside" (blue/grey chechered) the photoactivated region. These results are compared to separate control cultures that were not expressing PA-BoNT but treated with light (uninf-light) or cultures expressing vPA-BoNT but not locally illuminated (grey).

FIG. 4A Top shows a timeline of an experiment described herein. FIG. 4A Bottom is a schematic of viral injections. Two AAVs encoding vPA-BoNT N- and C-terminal fragments were bilaterally co-injected into the hippocampus. FIG. 4B is a representative image displaying expression of vPA-BoNT in the hippocampus. Brightfield, red [mCherry-IRES-SspBmicro-BoNT/B(C)], green [syph-GFP-BoNT/B(N)-iLID], and merged channel images are displayed. FIG. 4C is a schematic of ex-vivo recordings in acute hippocampal slices. Hippocampal CA1 axons were electrically stimulated to evoke AMPAR-mediated EPSCs in uninfected subicular pyramidal cells. FIG. 4D shows N- and C-terminal vPA-BoNT fragments expressed alone do not affect neurotransmission. Summary of evoked responses from slices prepared from uninfected (black), or singly infected animals (red, C-terminal fragment; green N-terminal fragment). Slices were illuminated after 10 min dark baseline with 473 nm light for 30s every min for 30 min. Right: Representative traces of averaged responses: Pre: 10 min baseline average, post: 15-30 min average. n refers to # of cells/# of animals, Error bars, SEM. FIG. 4E is a set of paired plots showing EPSC amplitudes recorded from individual cells pre- and post-light for uninfected (left), mCh-IRES-SspBmicro-BoNT(C) infected (middle) and syphGFP-BoNT(N)-iLID infected (right) animals. FIG. 4F shows a summary of evoked responses from slices prepared from animals infected with AAVs encoding both fragments of vPA-BoNT. Slices were either maintained in darkness (grey) or illuminated after 10 min dark baseline with 473 nm light for 30s every min for 30 min (blue). Right: Representative traces of averaged responses (pre: 10 min baseline average, post: 15-30 min average) for slices maintained in darkness (left traces) or treated with light (right traces). FIG. 4G is a set of paired plots of EPSC amplitudes averaged over the first 10 min (pre) and last 15 min (post) for individual dark (left) and light (right) treated cells. Similar light-evoked reductions in EPSC amplitudes were obtained using vPA-BoNTmilli (red) and or vPA-BoNTmicro (black). FIG. 4H shows a summary of the ratio of EPSC amplitudes measured before and after light exposure (or for slices maintained in darkness for the same time period) and for each condition in (FIG. 4D) and (FIG. 4F). Error bars, SEM, ****=p<0.0001, one-way ANOVA.

FIGS. 5A-5C illustrate reconstitution of split BoNT/B with iLID/SspB$_{nano}$. HEK293T cells were transfected with indicated split constructs and a GFP-VAMP-GST reporter and assayed for reporter cleavage after 28 hrs. Samples were either kept in the dark for the duration or exposed to blue light pulses (2s pulse, every 30s) for 4 hr before harvesting. BoNT(1-146)-iLID and BoNT(147-441, N157A)-SspB$_{nano}$. (FIG. 5A) or BoNT(147-441, N157A)-iLID and SspB$_{nano}$-BoNT(1-146) (FIG. 5B) showed minimal or no reconstitution of protease activity with light. In contrast, the configuration BoNT(1-146)-iLID with SspB-BoNT(147-441) (FIG. 5C) showed high levels of proteolytic activity. Using SspB$_{nano}$, significant dark background activity was observed.

FIG. 7A is a series of images of FM1-43 dye labeling in transfected neurons. Arrowheads indicate location of terminals. FIG. 7B shows quantification of FM1-43 dye loading in terminals. FM dye loading was normalized between values obtained from cells expressing full length BoNT/B (set at 0) and negative controls expressing mCh alone (set at 1). ***, p<0.0001, one-way ANOVA.

FIGS. 8A-8D illustrate the finding that PA-BoNT can be effectively reconstituted if either the N- or C-terminal BoNT/B fragment is localized to synaptic vesicles. FIG. 8A and FIG. 8C show quantification of VAMP2 staining in synaptic terminals from hippocampal neurons transfected with indicated constructs (schematics shown above). Experiments shown in FIG. 8A used synaptophysin-EGFP (syphGFP) attached at the N-terminus of SspBmilli-BoNT (147-441, Y365A), while those in FIG. 8C used syphGFP attached at the N-terminus of BoNT(N)-iLID(V416I). Cells were either kept in the dark (0 min) or exposed to blue light (1s pulse every 2 min) for the indicated times. Values were normalized between negative (mCh alone) and positive (mCh plus full length BoNT/B) controls. FIG. 8B and FIG. 8D show quantification of frequency and amplitude of quantal calcium transients in cultures infected with AAVs encoding the same syphGFP-fused constructs as in (respectively) FIG. 8A or FIG. 8C. Cells were exposed to 15, 30 and 60 min of blue light (blue) or kept in the dark (grey) or uninfected (black). Data are normalized to baseline (pre-blue light exposure) values.

FIGS. 9A-9C illustrate paired pulse analysis before and after activating vPA-BoNT. FIG. 9A shows sample PPR traces from primary neurons in subiculum, pre- and post-light exposure (left) or from cells maintained in the dark over the same time interval. FIG. 9B is a summary of PPRs from recordings made from uninfected slices and from infected slices expressing each component of vPA-BoNT/Bmicro individually and together, either prior to (pre) or 15-30 min following (post) light exposure. FIG. 9C shows expression of vPA-BoNT/Bmicro components individually and together does not affect basal PPR (compared to recordings made from uninfected animals) prior to light exposure.

DETAILED DESCRIPTION OF THE INVENTION

Definitions

Figure 1A:
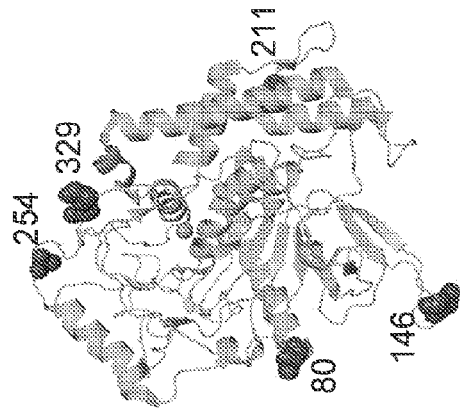

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5/6, even more preferably ±1%, and still more preferably ±0.1% from the specified value, as such variations are appropriate to perform the disclosed methods.

As used herein, "blue light" refers to any wavelength in the range of 400-495 nm.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

The term "therapeutic" as used herein means a treatment and/or prophylaxis. A therapeutic effect is obtained by suppression, remission, or eradication of a disease state.

To "treat" a disease as the term is used herein, means to reduce the frequency or severity of at least one sign or symptom of a disease or disorder experienced by a subject.

A "vector" or "expression vector" is a composition of matter which comprises an isolated nucleic acid and which can be used to deliver the isolated nucleic acid to the interior of a cell. A vector can comprise a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Numerous vectors are known in the art including, but not limited to, linear polynucleotides, polynucleotides associated with ionic or amphiphilic compounds, plasmids, and viruses. The term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

As used herein, the term "visible light" refers to any wavelength in the range of 400-700 nm.

As used herein, the Arabidopsis thaliana CIB1 protein (deltaNLS) has the amino acid sequence of SEQ ID NO:1:

```
        10         20         30         40
MNGAIGGDLL LNFPDMSVLE RQRAHLKYLN PTFDSPLAGF 50         60         70         80
FADSSMITGG EMDSYLSTAG LNLPMMYGET TVEGDSRLSI 90        100        110        120
SPETTLGTGN FKAAKFDTET KDCNEAAKKM TMNRDDLVEE 130        140        150        160
GEEEKSKITE QNNGSTKSIK KMKHKAKKEE NNFSNDSSKV 170        180        190        200
TKELEKTDYI HVRARRGQAT DSHSIAERVR REKISERMKF 210        220        230        240
LQDLVPGCDK ITGKAGMLDE IINYVQSLQR QIEFLSMKLA 250        260        270        280
IVNPRPDFDM DDIFAKEVAS TPMTVVPSPE MVLSGYSHEM 290        300        310        320
VHSGYSSEMV NSGYLHVNPM QQVNTSSDPL SCFNNGEAPS

330
MWDSHVQNLY GNLGV
```

As used herein, the CIBN(delta NLS) polypeptide has the amino acid sequence of amino acids 1-170 of SEQ ID NO:1 (hereby referred to as SEQ ID NO:2):

```
        10         20         30         40
MNGAIGGDLL LNFPDMSVLE RQRAHLKYLN PTFDSPLAGF 50         60         70         80
FADSSMITGG EMDSYLSTAG LNLPMMYGET TVEGDSRLSI 90        100        110        120
SPETTLGTGN FKAAKFDTET KDCNEAAKKM TMNRDDLVEE 130        140        150        160
GEEEKSKITE QNNGSTKSIK KMKHKAKKEE NNFSNDSSKV

170
TKELEKTDYI
```

As used herein, the Arabidopsis thaliana CRY2(deltaNLS) protein has the amino acid sequence of SEQ ID NO:3:

```
        10         20         30         40
MKMDKKTIVW FRRDLRIEDN PALAAAAHEG SVFPVFIWCP 50         60         70         80
EEEGQFYPGR ASRWWMKQSL AHLSQSLKAL GSDLTLIKTH 90        100        110        120
NTISAILDCI RVTGATKVVF NHLYDPVSLV RDHTVKEKLV 130        140        150        160
ERGISVQSYN GDLLYEPWEI YCEKGKPFTS FNSYWKKCLD 170        180        190        200
MSIESVMLPP PWRLMPITAA AEAIWACSIE ELGLENEAEK 210        220        230        240
PSNALLTRAW SPGWSNADKL LNEFIEKQLI DYAKNSKKVV 250        260        270        280
GNSTSLLSPY LHFGEISVRH VFQCARMKQI IWARDKNSEG 290        300        310        320
EESADLFLRG IGLREYSRYI CFNFPFTHEQ SLLSHLRFFP
```

-continued

```
         330        340        350        360
    WDADVDKFKA WRQGRTGYPL VDAGMRELWA TGWMHNRIRV 370        380        390        400
    IVSSFAVKFL LLPWKWGMKY FWDTLLDADL ECDILGWQYI 410        420        430        440
    SGSIPDGHEL DRLDNPALQG AKYDPEGEYI RQWLPELARL 450        460        470        480
    PTEWIHHPWD APLTVLKASG VELGTNYAKP IVDIDTAREL 490        500        510        520
    LAKAISRTRE AQIMIGAAPD EIVADSFEAL GANTIKEPGL 530        540        550        560
    CPSVSSNDQQ VPSAVRYNGS AAVKPEEEEE RDMKKSRGFD 570        580        590        600
    ERELFSTAES SSSSSVFFVS QSCSLASEGK NLEGIQDSSD

610
    QITTSLGKNG CK
```

As used herein, the *Botulinum* neurotoxin type B protease light chain has amino acid sequence of SEQ ID NO:4:

```
         10         20         30         40
    MPVTINNFNY NDPIDNNNII MMEPPFARGT GRYYKAFKIT 50         60         70         80
    DRIWIIPERY TFGYKPEDFN KSSGIFNRDV CEYYDPDYLN 90         100        110        120
    TNDKKNIFLQ TMIKLFNRIK SKPLGEKLLE MIINGIPYLG 130        140        150        160
    DRRVPLEEFN TNIASVTVNK LISNPGEVER KKGIFANLII 170        180        190        200
    FGPGPVLNEN ETIDIGIQNH FASREGFGGI MQMKFCPEYV 210        220        230        240
    SVFNNVQENK GASIFNRRGY FSDPALILMH ELIHVLHGLY 250        260        270        280
    GIKVDDLPIV PNEKKFFMQS TDAIQAEELY TFGGQDPSII 290        300        310        320
    TPSTDKSIYD KVLQNFRGIV DRLNKVLVCI SDPNININIY 330        340        350        360
    KNKFKDKYKF VEDSEGKYSI DVESFDKLYK SLMFGFTETN 370        380        390        400
    IAENYKIKTR ASYFSDSLPP VKIKNLLDNE IYTIEEGFNI 410        420        430        440
    SDKDMEKEYR GQNKAINKQA YEEISKEHLA VYKIQMCKSV K
```

As used herein, the LOV domain-peptide fusion (iLID) has the amino acid sequence of SEQ ID NO:5:

```
                EFLATTLERIEKNFVITDPR

LPDNPIIFASDSFLQLTEYS

REEILGRNCRFLQGPETDRA

TVRKIRDAIDNQTEVTVQLI

NYTKSGKKFWNVFHLQPMRD
```

```
                YKGDVQYFIGVQLDGTERLH

GAAEREAVCLIKKTAFQIAE

AANDENYF
```

As used herein, the *E. coli* SspB has the amino acid sequence of SEQ ID NO:6:

```
                EFSSPKRPKLLREYYDWLVD

NSFTPYLVVDATYLGVNVPV

EYVKDGQIVLNLSASATGNL

QLTNDFIQFNARFKGVSREL

YIPMGAALAIYARENGDGVM

FEPEEIYDELNIG
```

As used herein, the *E. coli* SspB$_{milli}$ has the amino acid sequence of SEQ ID NO:7

```
                EFSSPKRPKLLREYYDWLVD

NSFTPYLVVDATYLGVNVPV

EYVKDGQIVLNLSASVTGNL

QLTNDFIQFNAQFKGVSREL

YIPMGAALAIYARENGDGVM

FEPEEIYDELNIG
```

As used herein, the *E. coli* SspB$_{micro}$ has the amino acid sequence of SEQ ID NO:8

```
                EFSSPKRPKLLREYYDWLVD

NSFTPYLVVDATYLGVNVPV

EYVKDGQIVLNLSASATGNL

QLTNDFIQFNAQFKGVSREL

YIPMGAALAIYARENGDGVM

FEPEEIYDELNIG
```

As used herein, the *Botulinum* neurotoxin type A protease light chain has amino acid sequence of SEQ ID NO:9:

```
         10         20         30         40
    MPFVNKQFNY KDPVNGVDIA YIKIPNAGQM QPVKAFKIHN 50         60         70         80
    KIWVIPERDT FTNPEEGDLN PPPEAKQVPV SYYDSTYLST 90         100        110        120
    DNEKDNYLKG VTKLFERIYS TDLGRMLLTS IVRGIPFWGG 130        140        150        160
    STIDTELKVI DTNCINVIQP DGSYRSEELN LVIIGPSADI 170        180        190        200
    IQFECKSFGH EVLNLTRNGY GSTQYIRFSP DFTFGFEESL 210        220        230        240
    EVDTNPLLGA GKFATDPAVT LAHELIHAGH RLYGIAINPN 250        260        270        280
    RVFKVNTNAY YEMSGLEVSF EELRTFGGHD AKFIDSLQEN
```

```
         290        300        310        320
    EFRLYYYNKF KDIASTLNKA KSIVGTTASL QYMKNVFKEK 330        340        350        360
    YLLSEDTSGK FSVDKLKFDK LYKMLTEIYT EDNFVKFFKV 370        380        390        400
    LNRKTYLNFD KAVFKINIVP KVNYTIYDGF NLRNTNLAAN 410        420        430        440
    FNGQNTEINN MNFTKLKNFT GLFEFYKLLC VRGIITSKTK

SLDKGYNK
```

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides in one aspect light-controlled neurotoxin proteins. In certain embodiments, the invention includes methods of locally silencing neurons by administering a composition comprising AAV vectors carrying light-controlled neurotoxin fragments.

Regulated secretion is critical for diverse biological processes ranging from immune and endocrine signaling to synaptic transmission. Botulinum and tetanus neurotoxins, which specifically proteolyze vesicle fusion proteins involved in regulated secretion, have been widely used as experimental tools to block these processes. Genetic expression of these toxins in the nervous system has been a powerful approach for disrupting neurotransmitter release within defined circuitry, but their current utility in the brain and elsewhere remains limited by lack of spatial and temporal control. Herein, botulinum neurotoxin B was engineered so that it could be activated with blue light. Botulinum is a neurotoxin which causes paralysis, typically called botulism. The botulinum toxin has two domains: the light chain (also known as the catalytic domain) and the heavy chain. The heavy chain is responsible for neural docking and transmission of the light chain into the cell. The light chain is the active part of the toxin. Herein, the light chain was engineered into two pieces, the N-terminal fragment and the C-terminal fragment. The two fragments actively associate under light and become active.

The utility of this approach for inducibly disrupting excitatory neurotransmission was demonstrated, providing a first-in-class optogenetic tool for persistent, light-triggered synapse silencing. In addition to blocking neurotransmitter release, this approach has broad utility for conditionally disrupting regulated secretion of diverse bioactive molecules, including neuropeptides, neuromodulators, hormones and immune molecules.

In this work, a photoactivatable form of botulinum neurotoxin serotype B (BoNT/B) light chain protease was engineered. This serotype cleaves vesicle-associated membrane proteins (VAMPs) required for diverse forms of regulated secretion, including VAMP2/synaptobrevin involved in neurotransmitter release from inhibitory and excitatory neurons. Photoactivatable BoNT/B was activated by light to cleave VAMP2 in hippocampal neurons, leading to robust impairment of excitatory neurotransmitter release within minutes in intact circuits.

Compositions

In one aspect, the invention includes a light-controlled protein system. In certain embodiments, the system comprises a first construct comprising a first fragment of the protein, wherein the first fragment is fused to a first photodimerizer molecule. In other embodiments, the system comprises a second construct comprising a second fragment of the protein, wherein the second fragment is fused to a second photodimerizer molecule. In the absence of visible light, the first photodimerizer molecule does not bind to the second photodimerizer molecule, forming a non-activated system. In the presence of visible light, the first photodimerizer molecule binds to the second photodimerizer molecule, thus promoting physical contact between the first fragment of the protein and the second fragment of the protein, and forming an activated system. In certain embodiments, the biological activity of the protein in the activated system is higher than in the non-activated system.

In another aspect, the invention includes a composition comprising a first adeno-associated viral (AAV) vector comprising a nucleotide sequence encoding the amino acid sequence of the first construct of the invention, and a second AAV vector comprising a nucleotide sequence encoding the amino acid sequence of the second construct of the invention. In certain embodiments, the first and second vectors are the same. In other embodiments, the first and second vectors are distinct.

In certain embodiments, the visible light is blue or UV light.

In certain embodiments, the protein is a *Clostridium botulinum* neurotoxin, or a biologically active fragment thereof. In other embodiments, the *Clostridium botulinum* neurotoxin is serotype B (BoNT/B). In yet other embodiments, the first fragment of the light-controlled protein comprises an N-terminal portion of the neurotoxin light chain and the second fragment comprises a C-terminal portion of the neurotoxin light chain.

In certain embodiments, the photodimerizer molecule comprises the *Arabidopsis* photoreceptor cryptochrome 2 (CRY2) and the second photodimerizer molecule comprises the CRY2 interacting partner, CIBN. In other embodiments, the first photodimerizer molecule comprises a LOV domain-peptide fusion (iLID) and the second photodimerizer molecule comprises a domain of *E. coli* SspB. In yet other embodiments, the SspB comprises SspB$_{milli}$. In yet other embodiments, the iLID comprises a V416I mutation.

In certain embodiments, the first fragment comprises amino acid residues 1-146 of SEQ ID NO:4, and wherein the second fragment comprises amino acid residues 147-441 of SEQ ID NO:4.

In certain embodiments, the second fragment has at least one mutation selected from the group consisting of K94A, N157A, Y365A, and S311A/D312A in the corresponding residues of SEQ ID NO:4.

In certain embodiments, the protein further comprises a localization signal, e.g. a second protein that is fused to the protein and localizes it to a specific area, for example the synaptic vesicles. In other embodiments, the light-controlled protein is fused through the first or second fragment to a synaptophysin (Syph) protein.

In another aspect, the invention includes a composition comprising a first BoNT/B light chain fragment and a second BoNT/B light chain fragment. In certain embodiments, the first fragment comprises amino acid residues 1-146 of SEQ ID NO:4, and the second fragment comprises amino acid residues 147-441 of SEQ ID NO:4. The two fragments resulting from a split the BoNT/B light chain at amino acid 146/147, can assemble and be active on their own. These fragments can do not require a fused dimerizer to induce activity. When expressed on their own, they are non-functional, but when co-expressed in cells an active protein will reform that is functional.

In yet another aspect, the invention includes a composition comprising a first *botulinum* neurotoxin serotype A (BoNT/A) light chain fragment comprising amino acid residues 1-203 of SEQ ID NO:9 and a second BoNT/A light chain fragment comprising amino acid residues 203-448 of SEQ ID NO:9, wherein, when the first and second fragments are physically separate, a functional protein is not formed, and wherein, when the first and second fragments are physically adjacent, a functional protein is formed.

Methods of Treatment

As a non-limiting example, in this study the *botulinum* toxin catalytic domain was engineered to be activated with light. This is the active molecule in the widely-used 'Botox' which has many medical uses. The engineered version of Botox *botulinum* toxin described herein can be used to provide fine-tuned control over the toxin activity, using a focused beam of light to activate the toxin at precise locations and/or to titer the amount of toxin activity.

The compositions and methods of the present invention can be used to treat a variety of conditions currently treated by Botox, including but not limited to, involuntary muscle tightening, pain, migraines, and involuntary sweating.

In one aspect, the invention includes methods for locally silencing a neuron. Also included are methods of impairing neurotransmission and/or methods of light-triggered synaptic silencing and/or methods of disrupting vesicle cycling in presynaptic terminals.

In certain embodiments, the method comprises administering to a subject a composition comprising the light-controlled protein system of the invention. In certain embodiments, the light-controlled protein system comprises a first construct comprising a first protein fragment fused to a first photodimerizer molecule and a second construct comprising a second protein fragment fused to a second photodimerizer molecule. In certain embodiments, the light-controlled protein system comprises a first AAV vector comprising a nucleotide sequence encoding the amino acid sequence of the first construct and a second AAV vector comprising a nucleotide sequence encoding the amino acid sequence of the second construct of the invention. In certain embodiments, the first and second vector are administered to the subject. In certain embodiments, a third construct comprising a *botulinum* toxin heavy chain is administered to the subject. The third construct can be administered in the form of a purified protein or as a vector comprising a nucleotide sequence encoding the *botulinum* toxin heavy chain. Light is administered to the subject in a localized area. When light is administered, the first and second fragment dimerize and the neuron is silenced.

In certain embodiments, the light-controlled protein is a *Clostridium botulinum* neurotoxin, or a biologically active fragment thereof. In one embodiment, the *Clostridium botulinum* neurotoxin is serotype B (BoNT/B). In certain embodiments, the first fragment of the light-controlled protein comprises an N-terminal portion of the neurotoxin light chain and the second fragment comprises a C-terminal portion of the neurotoxin light chain. In certain embodiments, the photodimerizer molecule comprises the *Arabidopsis* photoreceptor cryptochrome 2 (CRY2) and the second photodimerizer molecule comprises the CRY2 interacting partner, CIBN. In certain embodiments, the first photodimerizer molecule comprises a LOV domain-peptide fusion (iLID) and the second photodimerizer molecule comprises a domain of *E. coli* SspB. In certain embodiments, the first fragment of the light-controlled protein comprises amino acid residues 1-146 of the neurotoxin light chain and the second fragment comprises amino acid residues 147-441 neurotoxin light chain. In certain embodiments, the light-controlled protein is fused through the first or second fragment to a synaptophysin (Syph) protein.

In certain aspects of the method, the subject is administered a composition comprising a first BoNT/B light chain fragment, a second BoNT/B light chain fragment, and a BoNT/B heavy chain. In certain embodiments, the first light chain fragment comprises amino acid residues 1-146 of SEQ ID NO:4, and the second light chain fragment comprises amino acid residues 147-441 of SEQ ID NO:4. The heavy chain and first and second light chain fragments can be expressed together or separately (e.g. in different cells). In certain embodiments, the first and second light chain fragments will self-complement. In certain embodiments, the methods of the invention include neuron-specific uses of the self-complementing toxin that silences neuronal activity.

The compositions of the present invention may be administered in a manner appropriate to the disease/condition to be treated (or prevented). The quantity and frequency of administration will be determined by such factors as the condition of the patient, and the type and severity of the patient's disease, although appropriate dosages may be determined by clinical trials. Compositions of the invention can be administered in dosages and routes and at times to be determined in appropriate pre-clinical and clinical experimentation and trials. Compositions may be administered multiple times at dosages within these ranges. Administration of the compositions of the invention may be combined with other methods useful to treat the desired disease or condition as determined by those of skill in the art.

It should be understood that the methods and compositions that would be useful in the present invention are not limited to the particular formulations set forth in the examples. The following examples are put forth so as to provide those of ordinary skill in the art with a complete disclosure and description of how to make and use the compositions of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Materials and Methods

Cloning and Mutagenesis.

TABLE 1

Oligos used in this study

| Oligo Name | SEQ ID | Sequence (5'-3') |
|---|---|---|
| 694R | SEQ ID NO: 10 | GGACCCACCACCTCCAGAGCCACCGCCACCATGAATATAATCCGTTTTCTCCAATTCC |
| 744F | SEQ ID NO: 11 | TCAACTCCAAGCTGGCCGCTCTAGAACTAGTGAGCTCGCCACCATGAAGATGGACAAAAAGACTATAGTTTG |
| 748F | SEQ ID NO: 12 | TCAACTCCAAGCTGGCCGCTCTAGAACTAGTGAGCTCGCCACCATGAATGGAGCTATAGGAGGTGA |
| 1702R | SEQ ID NO: 13 | TTAAGCGGCCGCCTCCTCCGGACCCACCACCTCCAGAGCCA |
| 1703F | SEQ ID NO: 14 | TTAAGGATCCGCGGCCGCATGCCAGTTACAATAAATAATTTTAATTATAATGATCCTATT |
| 1704R | SEQ ID NO: 15 | TTAAGAATTCCCGGGCTATTTAACACTTTTACACATTTGTATCTTATATACAGCC |
| 1707F | SEQ ID NO: 16 | TTAAGCGGCCGCACTAATGATAAAAAGAATATATTTTTACAAACAATGATCAAGT |
| 1708R | SEQ ID NO: 17 | TTAACCCGGGTCAATTTAAGTAATCTGGATCATAATATTCACAAACATCT |
| 1727F | SEQ ID NO: 18 | TTAAGCGGCCGCGCAAGTATATTTAATAGACGTGGATATTTTC |
| 1728R | SEQ ID NO: 19 | TTAACCCGGGTCAGCCTTTGTTTTCTTGAACATTATTAAATACGC |
| 1729F | SEQ ID NO: 20 | TTAAGCGGCCGCGAAGTGGAGCGAAAAAAAGGTATTTTCG |
| 1730R | SEQ ID NO: 21 | TTAACCCGGGTCATCCTGGATTACTGATTAATTTATTAACAGTTACAC |
| 1735F | SEQ ID NO: 22 | TTAAGCGGCCGCAAATTTTTTATGCAATCTACAGATGCTATACAGG |
| 1736R | SEQ ID NO: 23 | TTAACCCGGGTCATTTTTCATTTGGTACAATTGGTAAATCATCTACT |
| 1740F | SEQ ID NO: 24 | TTAAGAGCTCGCCACCATGCCAGTTACAATAAATAATTTTAATTATAATGATCCTATT |
| 1794F | SEQ ID NO: 25 | TTAAACCGGTCGCCACCA |
| 1795R | SEQ ID NO: 26 | TTAAGCGGCCGCCTCCTCCTGAACCTCCACCCGCGGAAGAGACAACCCACACGATG |
| 1811F | SEQ ID NO: 27 | TTAAGCGGCCGCATGACCAAGTTACCTATACTAGGTTATTG |
| 1812R | SEQ ID NO: 28 | TTAATCTAGACTCAAACCAGATGATCCGATTTTG |
| 2009F | SEQ ID NO: 29 | TTAACTCGAGCCACCATGCCAGTTACAATAAATAATTTTAATTATAATGATCCT |
| 2010R | SEQ ID NO: 30 | TTAAGCGGCCGCCTCCTGGATTACTGATTAATTTATTAACAGTTACAC |
| 2011F | SEQ ID NO: 31 | GTGGCGGTGGCTCTGGAGGTGGGTCCGAGCTCGGGGAGTTTCTGGCAACC |
| 2012F | SEQ ID NO: 32 | TTAAGCGGCCGCAGCGGTGGCGGTGGCTCTGG |
| 2013R | SEQ ID NO: 33 | TTAACCCGGGCTTAAGTCAAAAGTAATTTTCGTCGTTCGCTGC |
| 2014F | SEQ ID NO: 34 | TTAACTCGAGCCACCATGGAAGTGGAGCGAAAAAAAGGTATTTTCG |
| 2015R | SEQ ID NO: 35 | TTAATCCGGAGCCGCCACCTTTAACACTTTTACACATTTGTATCTTATATACAGCC |
| 2016F | SEQ ID NO: 36 | TTAATCCGGAGGCGGTGGCTCTGGAGGTGGGTCCGAATTCAGCTCCCCGAAACGC |
| 2017R | SEQ ID NO: 37 | TTAACCCGGGATATCTCAACCAATATTCAGCTCGTCATAGATTTCT |

TABLE 1-continued

Oligos used in this study

| Oligo Name | SEQ ID | Sequence (5'-3') |
|---|---|---|
| 2053F | SEQ ID NO: 38 | TTAAGAATTCCTGGCAACCACACTGGAAC |
| 2054F | SEQ ID NO: 39 | TTAACTCGAGGCCACCATGGAATACAGCTCCCCGAAACGC |
| 2055R | SEQ ID NO: 40 | CACCACCTCCAGAGCCACCGCCACCGAGCTCAATATTCAGCTCGTCATAGATTTCTTCTG |
| 2167F | SEQ ID NO: 41 | TTAAAGATCTGCTAGCGCCACCATGGTGAGCAAGGGCGAG |
| 2168R | SEQ ID NO: 42 | TTAAGAATTCATTTAACACTTTTACACATTTGTATCTTATATACAGCCA |
| 2169R | SEQ ID NO: 43 | TTAAGAATTCAAAAGTAATTTTCGTCGTTCGCTGCC |
| 2216F | SEQ ID NO: 44 | TTAAGCTAGCGCCACCATGGACGTGGTGAATCAGCTG |
| 2217R | SEQ ID NO: 45 | TTAAGTCGACAGCGTAATCTGGAACATCGTATGGGTACTTGTACAGCTCGTCCATGCC |
| 2218R | SEQ ID NO: 46 | TTAGTCGACCCAGATCCTCTTCTGAGATGAGTTTTTGTTCCTTGTACAGCTCGTCCATGC |

To generate CRY2- and CIBN-fused N- and C-terminal BoNT/B LC fragments, CRY2 and CIBN were first replaced in mCherry-IRES-CRY2-CreN and mCherry-IRES-CIBN-CreC (Taslimi, A. et al., 2016, Nat. Chem. Biol. 12, 425-30) with NLS (nuclear localization sequence)-deleted versions. CRY2(ΔNLS) was PCR-amplified using oligos 744F (SEQ ID NO: 11)/1702R (SEQ ID NO: 13), and CIBN(ΔNLS) was amplified using oligos 748F (SEQ ID NO:12)/694R (SEQ ID NO: 10), followed by 748F (SEQ ID NO:12)/1702R (SEQ ID NO: 13). Next, the Cre fragments were removed at Not I and Xma I sites, and replaced by BoNT/B light chain N-terminal or C-terminal fragments. For the full-length positive control (pQL24, mCh-IRES-BoNT/B), BoNT/B was amplified (1740F (SEQ ID NO:24)/1704R (SEQ ID NO: 15)) and cloned into mCherry-IRES-CRY2(ΔNLS)-CreN between Sac I and Xma I sites. To generate the EGFP-VAMP-GST reporter (pQL47), pEGFP-VAMP3 (Addgene 42310) was PCR-amplified (oligos 1794F (SEQ ID NO:25)/1795R (SEQ ID NO: 26)) to add a linker between VAMP3 and Not I site. GST was PCR-amplified (oligos 1811F(SEQ ID NO:27/1812R (SEQ ID NO: 28)) to add Not I and Xba I sites, and inserted after the linker. Mutations in BoNT/B-LC and iLID were introduced by one-step Phusion mutagenesis using protocols from New England Biolabs. Briefly, non-overlapping oligos containing desired mutations were used to amplify the entire plasmid using Phusion High-Fidelity DNA Polymerase (NEB), then the PCR products were treated by T4 Polynucleotide Kinase (NEB, M020i S) in the presence of ATP at 37° C. for 30 min before self-ligation using T4 Quick Ligase (NEB).

To generate mCh-IRES-BoNT(1-146)-iLID (pQL155), CRY2 was first replaced in pQL7 with BoNT(1-146) (oligos 2009F (SEQ ID NO:29)/2010R (SEQ ID NO:30)) at Xho I and Not I sites. Next, iLID (amplified from Venus-iLID-Mito, Addgene 60413, oligos 2011F (SEQ ID NO:31)/2013R (SEQ ID NO:33)/then 2012F(SEQ ID NO:32)/2013R (SEQ ID NO:33)) was inserted between Not I and Xma I sites. Similarly, for mCh-IRES-BoNT(147-441, N157A)-SspB$_{nano}$ (pQL162), CRY2 in pQL7 was first replaced with BoNT(147-441, N157A) (amplified using oligos 2014F(SEQ ID NO:34)/201SR (SEQ ID NO:35)) at Xho I and BspEI sites. SspB$_{nano}$ (PCR-amplified from tgRFPt-SspB-WT, Addgene 60415, oligos 2016F (SEQ ID NO:36)/2017R (SEQ ID NO:37) was inserted between BspEI and Xma I sites. For mCh-IRES-BoNT/B(147-441, N157A)-iLID (pQL176), SspB$_{nano}$ in pQL162 was removed between EcoRI and Xma I sites, then replaced by iLID (PCR-amplified using oligos 2053F(SEQ ID NO:38)/2013R (SEQ ID NO:33)). To generate SspB-BoNT(1-146) and SspB-BoNT(147-441), SspB$_{nano}$ (Addgene 60415), SspB$_{micro}$ (Addgene 60416), or SspB$_{milli}$ was PCR-amplified using oligos 2054F (SEQ ID NO:39)/2055R (SEQ ID NO:40) and cloned into pQL7, pQL17, pQL54, or pQL56 between Xho I and BspEI sites.

All AAV plasmids were propagated in Stbl3 *E. coli* (Invitrogen). To generate pQL262 (pAAV-hSYN-mCh-IRES-BoNT(1-146)-iLIDv$_{4161}$), mCh-IRES-BoNT(1-146)-iLID$_{v4161}$ was PCR-amplified from pQL193 (oligos 2167F (SEQ ID NO:41Y2169R (SEQ ID NO:43)) to add Bgl II and EcoRI sites, and then cloned into pAAV-hSYN-mRuby (derived from pAAV1-hSYN-mGFP-2A-synaptophysin-mRuby, by inserting mRuby into AAV-hSYN at EcoRI and BamHI sites, oligos mRubyF/mRubyR) between BamHI (removed) and EcoRI sites. Similarly, to generate pQL269 [pAAV-hSYN-mCh-IRES-SspB$_{micro}$-BoNT(147-441, Y365A)] and pQL261 [pAAV-hSYN-mCh-IRES-SspB$_{milli}$-BoNT(147-441, Y365A)], mCh-IRES-SspB$_{micro}$-BoNT (147-441, Y365A) and mCh-IRES-SspB$_{milli}$-BoNT(147-441, Y365A) were amplified from pQL173 and pQL185 (oligos 2167F(SEQ ID NO:41)/2168R (SEQ ID NO:42)) and inserted into pAAV-hSYN-mRuby in the same way. To generate synaptophysin-tagged versions (pQL280, pAAV-hSYN-syph-EGFP-HA-SspB$_{milli}$-BoNT(147-441, Y365A); pQL281, pAAV-hSYN-syph-EGFP-myc-BoNT(1-146)-iLIDV416I), synaptophysin-EGFP was PCR-amplified using 2216F (SEQ ID NO:44)/2217R (SEQ ID NO:45) or 2216F (SEQ ID NO:44)/2218R (SEQ ID NO:46) to add a Nhe I site, Sal II site and HA or myc tag, then cloned into pQL261 or pQL262 between Nhe I and Sal II. The combination of constructs designated sPA-BoNT$_{micro}$ consists of (pQL269+pQL262), sPA-BoNT$_{milli}$ is (pQL261+pQL262), vPA-BoNT$_{micro}$ consists of (pQL269+pQL281), and sPA-BoNT$_{milli}$ consists of (pQL261+pQL281).

Characterization of Split BoNT/B in HEK293T Cells.

HEK293T cells were maintained in Dulbecco's modified Eagle medium (DMEM) supplemented with 10% FBS at 37° C. with 5% CO2. To test split constructs, 1 μg of the GFP-VAMP-GST cleavage reporter and each BoNT/B fragment were transfected into HEK293T cells on 12-well plates using standard calcium phosphate transfection methods.

Cells were wrapped in aluminum foil after transfection and kept in dark for 24 hr before blue light treatment (461 nm delivered from a custom-built LED array). For CRY2/CIBN systems, 2 s pulses were delivered every 3 min; for iLID/SspB systems, 1 s pulses were delivered every 30 s, unless noted otherwise. Dark samples were kept in the dark throughout the experiment. Cells were harvested after 4-5 hours of light treatment, unless specified otherwise (28-29 hrs post transfection). For harvest, cells were washed in 1×PBS, collected, and lysed in 2× Laemmli sample buffer with boiling. Proteins were separated by electrophoresis on an SDS-PAGE gel and transferred to nitrocellulose membranes, followed by probing with primary (anti-EGFP, Sigma G1544) and secondary (goat anti-rabbit IR-Dye 800CW, LiCOR, 926-3221) antibodies. An Odyssey FC Imager (Li—COR) was used to visualize labeled immunoblots.

Neuronal Cell Culture.

Primary hippocampal neurons were prepared from neonatal Sprague-Dawley rats. Hippocampi were dissected from the brains of postnatal day 0-2 rats and dissociated by papain digestion. Neurons were plated at 150,000 cells/well in MEM, 10% FBS (Hyclone) containing penicillin/streptomycin on poly-d-lysine-coated 18 mm coverslips. After 1 d the media was replaced with Neurobasal-A supplemented with B27 (Invitrogen) and GlutaMAX (MermoFischer). The neurons were then fed with Neurobasal-A, B27, and mitotic inhibitors (uridine+fluoro-deoxyuridine [Ur+FdUr]) by replacing half the media on day 5 or day 6 and then weekly. Neurons were maintained at 37° C. in a humidified incubator at 5% $Co_2$. Neurons were transfected with 0.75 µg of each split construct using Lipofectamine 2000 (Invitrogen) according to the manufacturer's recommendations and allowed to express for 48-72 hours.

Live Cell Imaging.

Live cell imaging of dissociated neurons was carried out at 34° C. on an Olympus IX71 equipped with a spinning disc scan head (Yokogawa). Excitation illumination was delivered from an acousto-optic tunable filter (AOTF) controlled laser launch (Andor). Images were acquired using a 60× Plan Apochromat 1.4 NA objective, and collected on a 1024×1024 pixel Andor iXon EM-CCD camera. Data acquisition and analysis were performed with Metamorph (Molecular Devices) and ImageJ software.

Measurement of Endogenous VAMP2 Cleavage in Neurons.

Cultured hippocampal neurons were transfected with PA-BoNT or full length BoNT/B or mCherry alone and allowed to express for 48 hours in the dark. Cells were fixed in the dark or following exposure to blue light, permeabilized with 0.1% Triton-X100 and blocked with 5% BSA. Cells were incubated with a primary antibody against VAMP2 (Synaptic Systems, 104211) that does not recognize VAMP2 following cleavage by BoNT/B, followed by goat-anti-Mouse Alexa Fluor 647 secondary antibody (Invitrogen, A-32728). The amount of VAMP2 staining in presynaptic boutons was compared to neighboring untransfected neurons and normalized to positive (full length BoNT/B) and negative (mCherry alone) controls.

$Ca^{2+}$ Imaging and Analysis.

To image quantal $Ca^{2+}$ transients (QCTs), neurons transfected with jRGECO1a and infected with AAVs expressing PA-BoNT were incubated in an artificial cerebro-spinal fluid (ASCF) solution containing (in mM): 130 NaCl, 5 KCl, 10 HEPES, 30 glucose, 2.5 $CaCl_2$, 0.03 glycine and 0.002 tetrodotoxin (Tocris) (pH 7.4). Single z-plane images of a portion of the dendritic arbor were acquired at 7 Hz for 1 min to record baseline QCTs. Cells were then either exposed to 488 nm light every two min or kept in the dark. The same z plane was then imaged again to record QCTs post-treatment.

To measure the frequency and amplitude of QCTs, regions of interest (ROIs) were drawn around 12 clearly resolved spines per cell in the baseline movie. The ROIs were saved and the same synapses were analyzed in the post-treatment movies. The mean background-subtracted jRGECO1a fluorescence within each ROI was measured. A baseline of 10 frames was established and each frame was compared to that baseline. A threshold of a 40% increase in fluorescence over baseline was established to remove small variations in fluorescence. Event frequency and average peak amplitudes were compared between baseline and time points after blue light-treatment.

Electrophysiology in Primary Culture.

Dissociated hippocampal neurons infected with AAVs expressing PA-BoNT were either kept in the dark or exposed to at least 1 h of blue light (is pulse every 2 min). Whole cell voltage clamp recordings were carried out from dissociated hippocampal neurons (DIV 17-19) bathed in (mM): 10 HEPES, 130 NaCl, 5 KCl, 30 D-glucose, 2 $CaCl_2$ and 1 $MgCl_2$ supplemented with 1 µM tetrodotoxin and 30 µM bicuculline (Tocris). Intracellular solution contained (in mM): 130 cesium methanesulfonate, 3 $Na_2ATP$, 0.5 $Na_3GTP$, 0.5 EGTA, 10 phosphocreatine, 5 $MgCl_2$, 2.5 NaCl, 10 HEPES (290-300 mOsm). The pH was adjusted to 7.25 with CsOH. Data were collected using a multiclamp 700b amplifier and digitized using a National Instruments DAQ board at 10 KHz and filtered at 2 KHz (single pole Bessel filter) and collected with WinLTP software (University of Bristol). Data were analyzed using WinLTP (University of Bristol), the NeuroMatic package in IGOR Pro (WaveMetrics) and Mini Analysis software (Synaptosoft).

FM Dye Loading Experiments.

Dissociated hippocampal neurons were transfected with PA-BoNT or full length BoNT/B or mCherry and allowed to express for 48 hours. Neurons were either kept in the dark or exposed to blue light (Is blue light every 2 min) for indicated times, then surface membrane was saturated with FM1-43FX (5 µM) in ACSF containing 10 µM NBQX and 100 µM APV. Cells were exposed to 50 mM KCl (in the presence of NBQX/APV) for one minute to induce exocytosis then returned to baseline ACSF containing FM1-43FX for 5 min to allow for compensatory endocytosis. Surface fluorescence was quenched with 1 mM Advasep7 and cells were fixed and imaged. To quantify FM dye uptake, fluorescence within presynaptic boutons of transfected cells was measured and compared to dye uptake of neighboring untransfected cells. Values were then normalized between positive (full length BoNT/B) and negative (mCherry alone) controls.

Production of AAVs for Primary Culture and In Vivo Injection.

AAV-DJ expressing PA-BoNT constructs were generated as previously described. Briefly, HEK293T cells were co-transfected with the AAV vector along with helper plasmids (pDJ and pHelper) using calcium phosphate transfection. 72 hours post-transfection cells were harvested, lysed and purified over an iodixanol gradient column (2 hours at 63,500 r.p.m. in a Beckman Type80Ti rotor). Virus was dialyzed to remove excess iodixanol and aliquoted and stored at −80° C. until use.

Stereotactic Viral Injection.

P21 C57BL6J male and female mice were anesthetized with an intraperitoneal injection of 2,2,2-Tribromoethanol (250 mg/kg) then head fixed to a stereotactic frame (KOPF).

An incision was made in the scalp with sterilized scissors, and small holes (~0.5 mm diameter) were drilled into the skull using a handheld dental drill. Viral solutions containing either AAV1-hSYN-mCherry-IRES-SspB$_{micro/milli}$-BoNT/B (C),AAV1-hSYN-syph-GFP-BoNT/B(N)-iLIDV416i, or a premixed solution of both, were injected into each hemisphere with a pulled glass micropipette. Using a syringe pump (World Precision Instruments), a total volume of 0.8-1.0 μL was delivered into intermediate CA1 at an infusion rate of 14 μL/hr at the following coordinates: AP: −3.2, M/L: f 3.45 (relative to Bregma), and DN: −2.5 (relative to pia). The micropipette was held in place for 5 min after injection to prevent backflow of virus, then slowly retracted. Correct localization and expression of viral infection was verified post-hoc by presence of mCherry and/or GFP.

Electrophysiology in Acute Slices.

At P34-P40, animals were deeply anesthetized with isoflurane and decapitated. Brains were rapidly dissected and 300 μm horizontal slices were sectioned with a vibratome (Leica VT1200) in ice cold, oxygenated solution containing (in mM) 85 NaCl, 75 sucrose, 25 D-glucose, 24 NaHCO$_3$, 4 MgCl$_2$, 2.5 KCl, 1.3 NaKPO$_4$ and 0.5 CaCl$_2$. Slices were then allowed to recover for 30 min in oxygenated ACSF at 31.5° C. containing (in mM) 126 NaCl, 26.2 NaHCO$_3$, 11 D-Glucose, 2.5 KCl, 2.5 CaCl$_2$ 1.3 MgSO$_4$.7H$_2$O, and 1 NaKPO$_4$ before resting at room temperature for at least 1 hour. Slices were superfused in ACSF containing 100 μM picrotoxin and 50 μM D-AP5. Subicular pyramidal neurons were visually identified with an Olympus BX51W microscope with a 40× dipping objective collected on a Hamamatsu ORCA-Flash 4.0 V3 digital camera using an IR bandpass filter. Cells were patched in whole cell configuration using glass pipettes pulled to a resistance of 3-5 mQ and filled with an internal solution containing (in mM) 117 Cs-methanesulfonate, 15 CsCl, 10 HEPES, 10 Phosphocreatine, 10 TEA, 8 NaCl, 4 Mg-ATP, 1 MgCl$_2$, 0.5 GTP, and 0.2 EGTA. AMPAR-mediated EPSCs were evoked by electrically stimulating CA1 axon efferents within the alveus/stratum oriens at the border of CA1 and subiculum at 0.1 Hz with a homemade Nichrome electrode. Stimulus intensity was adjusted to evoke 50-300 pA AMPAR-mediated EPSCs and baseline was acquired for 10 min before photoactivation of split toxins using 473 nm blue light. Slices were illuminated with blue light pulses for 30 min (30s every min). Release probability was assessed before and after the 40 min recording (10 min baseline+30 min light treatment) by measurements of paired pulse ratios at inter-stimulus intervals of 33 ms. Slices were then fixed in 4% PFA then mounted for posthoc imaging to validate expression of each split toxin. All experiments were performed using a Multiclamp 700B amplifier and a Digidata 1440 or 1550B digitizer. Recordings were collected using a 2 kHz lowpass filter and digitized at 10 kHz. All slice preparations and baseline recordings were performed in the dark using red LED illumination and under infrared optics to prevent inadvertent photoactivation of PA-BoNT.

Statistical Analysis.

Statistical significance for experiments comparing two populations was determined using a two-tailed unpaired Student's t-test. In cases where the two populations represented paired measurements, a paired Student's t-test was used. For experiments comparing three or more populations, a one-way ANOVA with Bonferroni multiple comparison test was used. All statistical analyses were performed using Graphpad Prism (Graphpad Software, Inc.). Data are presented as mean f SEM unless otherwise noted.

The results of the experiments are now described.

Figure 1B:
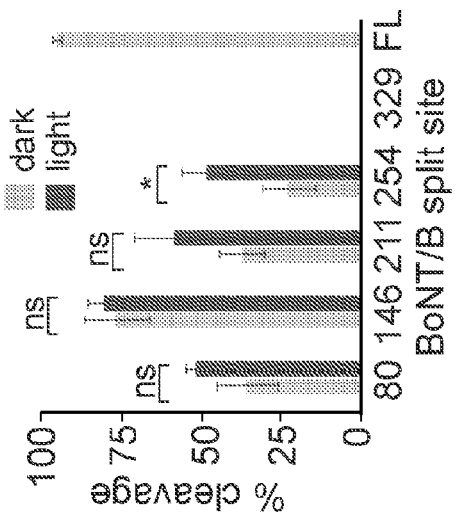
Figure 1C:
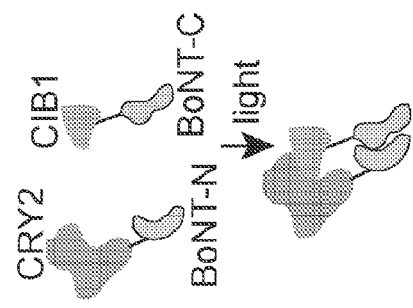

Example 1: A Photoactivatable *Botulinum* Neurotoxin for Inducible Control of Neurotransmission The light chain of *Clostridium botulinum* neurotoxin type B (BoNT/B-LC, amino acids 1-441) is a ~50 kD endoprotease that forms a compact catalytic core. To regulate BoNT/B-LC (hereafter, BoNT/B) protease activity with light, a split protein complementation approach was used, wherein a protein is split into two fragments that can be functionally reconstituted when fused to inducible protein dimerizer modules (FIG. 1A). BoNT/B was split at solvent-exposed loops to minimize disturbance to the protein structure, targeting five initial sites (FIG. 1B). To assay protease activity, a 68 kDa GFP-VAMP-GST reporter was generated that yields a 33 kDa fragment when cleaved by BoNT/B. Co-expression of full length BoNT/B resulted in near-complete conversion of the full length reporter to the smaller cleavage product (FIG. 1C, left panel).

Figure 1D:
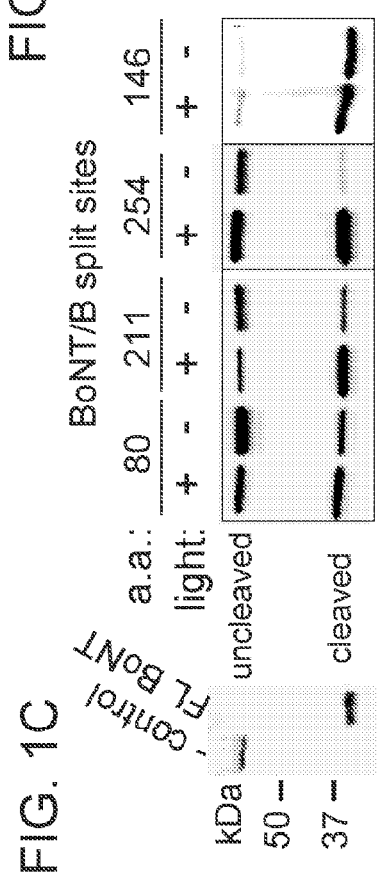

To conditionally reconstitute BoNT/B, N- and C-terminal BoNT/B fragments were fused to NLS-deleted versions of *Arabidopsis* photoreceptor cryptochrome 2 (CRY2) and its binding partner CIBN (residues 1-170 of *Arabidopsis* CIB1), which dimerize upon blue light exposure (Kennedy et al., 2010 Nature Methods 7, 973-975). CRY2 and CIBN-fused BoNT fragments were expressed in HEK293T cells along with the BoNT/B activity reporter. Reporter cleavage was monitored in cells maintained in the dark or after four hours of light exposure. Of five split sites tested, one site (split at residue 254) showed significant light-regulated activity (FIGS. 1C-1D), while one site (329) showed no activity in light or dark (FIG. 1D). BoNT/B split at residue 146/147 showed minimal light dependence but near-complete reporter cleavage even in dark (76.4±4.8% cleavage in dark, 80.3±10.4% in light) (FIGS. 1C-1D), indicating these fragments reassemble into an active enzyme independent of the fused dimerizer modules.

The 146/147 split fragments were chosen for further manipulation, given the potent activity of BoNT/B split at this location. Mutations were sought that are in the interface between the two fragments that reduce affinity sufficiently to block fragment self-assembly, but allow reconstitution of activity upon induction of photodimerizer interaction with light. Analysis of the crystal structure of intact BoNT/B light chain revealed extensive electrostatic and hydrogen bonding interactions at the interface between BoNT/B(1-146) and BoNT/B(147-441) (FIG. 1E). Four interface-disrupting mutations (K94A, N157A, Y365A, and S311A/D312A) showed greatly reduced dark activity yet could be activated to varying degrees with light (FIG. 1F).

In parallel with the CRY2/CIBN dimerizers for reconstitution of split BoNT/B, specific limitations for viral packaging (e.g. the large size of the CRY2 photoreceptor), motivated the testing of other photodimerizer systems. The iLID/SspB photodimerizer system uses smaller fusions—an engineered LOV domain-peptide fusion (AsLOV2-SsrA, 'iLID') and a domain of *E. coli* SspB—that are triggered to interact with blue light. In addition to their smaller size, the iLID/SspB system has been engineered for dynamic light control over a range of expression levels by generating mutations in SspB that reduce affinity to LOV2-SsrA. In testing the 146/147 split fragments in the iLID/SspB system, the optimal fusion configuration was found to be BoNT(N)-iLID and SspB-BoNT(C), with other N- and C-terminal configurations not functional (FIG. 5). Initial studies used SspB$_{nano}$, which binds with high affinity to iLID even in dark (binding affinity 4.7 µM in dark, 132 nM in light), and yielded high background with minimal light-dependent differences in cleavage activity (FIG. 5C). Substituting SspB$_{milli}$, a lower affinity version (binding affinity>1 mM dark, 56 µM in light), robust light/dark differences were observed (FIG. 1G). As the wild-type AsLOV2 domain used to generate the iLID component has a short photoactivation lifetime (half-life ~27 s), a mutation (V416I, using AsLOV2 domain nomenclature) previously found to slow the dark reversion rate ~10-fold, enabling use of less frequent light pulse treatments in neurons, was added (FIG. 1H).

Example 2: Split BoNT Cleaves VAMP2 and Impairs Neurotransmitter Release

Figure 6:
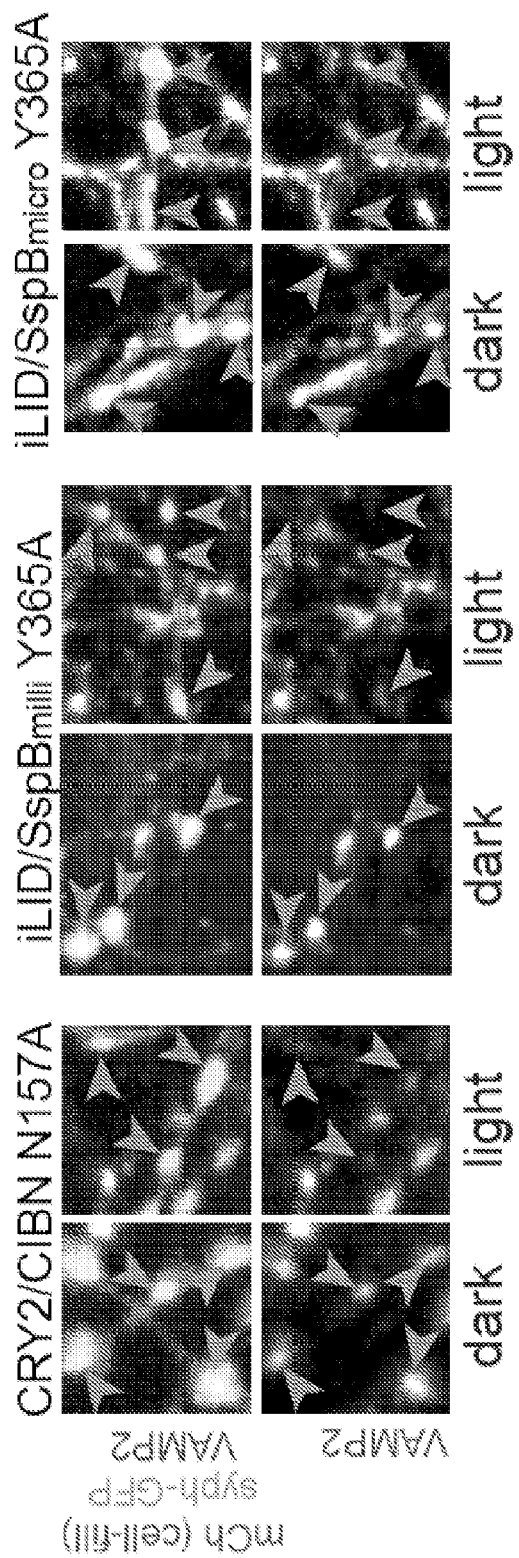
FIG. 6 illustrates light-induced cleavage of endogenous VAMP2 in neurons with split BoNT/B. Representative VAMP2 staining in presynaptic terminals (labeled by expressed syph-GFP, pink arrowheads) from neurons transfected with (from left to right): CRY2/CIBN BoNT (N157A) dark, light; iLID/SspBmilli BoNT(Y365A) dark, light; iLID/SspBmicro BoNT(Y365A) dark, light. All versions used BoNT split at residue 146/147. Note that the expressed toxin is only present in the transfected axons labeled with mCh and GFP-syph. Light treated neurons were exposed to blue light (is pulse every 2 min) for 4 h. Quantification is provided in FIG. 2A.

Three top candidates from the initial screening in HEK293T cells, CRY2/CIBN BoNT/B K94A and N157A, and iLID/SspB$_{milli}$ Y365A (using BoNT/B fragments split at 146/147), were chosen for characterization of endogenous vesicle associated membrane protein 2 (VAMP2) cleavage in dissociated hippocampal neurons. As proteins expressed in neurons or delivered through viral transduction are expressed at much lower levels than in HEK293T cells, the medium-affinity iLID/SspB$_{micro}$ pair was also tested. Dimerizer-fused BoNT fragments were transfected along with syph-GFP as a marker of presynaptic terminals, and cells were exposed to dark or light for four hours. Neurons were fixed and immunostained for endogenous VAMP2 using a monoclonal antibody that labels full-length VAMP2 but does not recognize BoNT/B VAMP2 cleavage products. Neurons transfected with mCherry (mCh) alone, or mCh plus intact full length BoNT/B light chain, served as negative and positive controls respectively. Cells expressing the full-length BoNT/B showed nearly undetectable levels of VAMP2 (FIG. 2A). The CRY2/CIBN K94A and N157A variants and iLID/SspB$_{milli}$ Y365A showed VAMP2 levels in the dark equivalent to the negative control (FIG. 2A, FIG. 6). Use of SspB$_{micro}$ resulted in decreased dark levels of VAMP2 staining (70±5% relative to negative control) indicating some background activity. Light exposure resulted in a substantial loss of VAMP2 immunoreactivity for all variants tested except CRY2/CIB K94A, which showed no activity against endogenous VAMP2 (FIG. 2A). The kinetics of VAMP2 cleavage for iLID/SspB Y365A milli and micro SspB variants are shown in FIG. 2B.

Figure 7B:
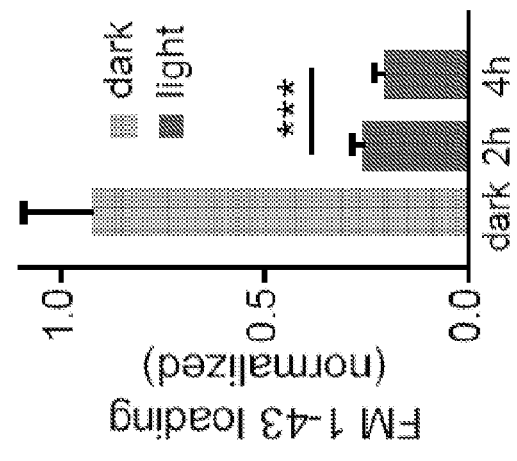
FIGS. 7A-7B illustrate the finding that split BoNT reconstituted with iLID dimerizers disrupts presynaptic vesicle trafficking. Cultured hippocampal neurons were transfected with sPA-BoNTmicro [mCh-IRESBoNT(1-146)-iLID (V416I) and mCh-IRES-SspBmicro-BoNT(147-441, Y365A)] or indicated negative or positive controls (mCherry alone, or mCherry with full length BoNT). Cells were maintained in darkness or exposed to 2 or 4 hrs of blue light pulses (is pulse every 2 min) prior to FM1-43 dye loading experiments.
Figure 7A:
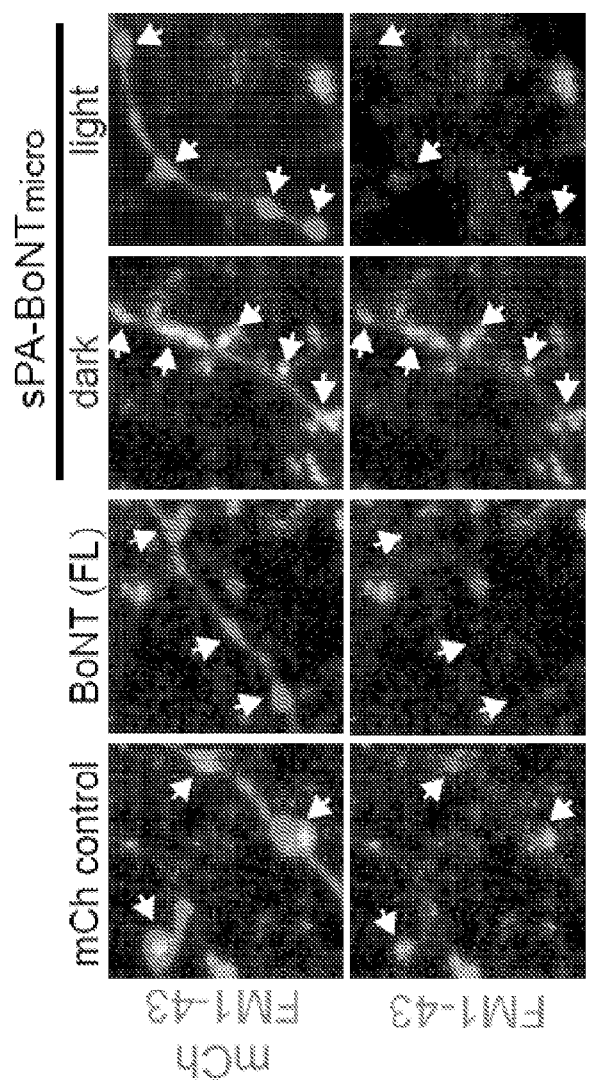

While light activated toxins cleaved a significant fraction of VAMP2, any remaining uncleaved VAMP2 could still contribute to vesicular trafficking. Indeed, only one to three SNARE complexes are sufficient to drive vesicle fusion. Thus, it was functionally tested whether iLID/SspB variants could impair neurotransmitter release in a light-dependent manner. First measured was vesicle fusion and subsequent uptake of the styryl fluorescent dye FM1-43 into presynaptic terminals of cultured hippocampal neurons. Neurons were transfected with iLID/SspB$_{micro}$ Y365A BoNT fragments and either maintained in the dark or pre-exposed to 2 or 4 hours of blue light (is pulse every 2 min). FM1-43 uptake triggered by a brief (60 s) exposure to a high (50 mM) isosmotic extracellular K$^+$ solution was then assessed. Neurons expressing both constructs but maintained in darkness displayed activity-triggered FM1-43 uptake that was nearly identical to that of control neurons (FIGS. 7A-7B). Two hours following onset of light exposure, FM1-43 uptake was reduced ~4-fold, demonstrating that this approach can robustly disrupt vesicle cycling in presynaptic terminals (FIGS. 7A-7B).

Based on these results, adeno-associated viral vectors containing the BoNT(1-146)-iLIDV416I and SspB-BoNT (147-441, Y365A) combination, hereafter referred to as soluble PA-BoNT (sPA-BoNT), were generated. Because protein expression from viral vectors is likely to be lower than in transiently transfected cells, both SspB$_{milli}$ and SspB$_{micro}$ variants were tested. To confirm the efficacy of the virally delivered BoNT, spontaneous miniature excitatory postsynaptic currents (mEPSCs) were measured from viral-transduced dissociated hippocampal cultures. Based on the kinetics of sPA-BoNT VAMP2 cleavage, neurons were exposed to blue light (1s pulse every 2 min) for at least 1h (and no more than 4h) to achieve maximum depletion of VAMP2 prior to mEPSC recordings. Following exposure of cells expressing sPA-BoNTi$_{micro}$ (using SspB$_{micro}$) to blue light, a 2-fold reduction in the frequency (2.76±0.447 sec~, dark vs 1.460±0.350 sec$^1$, light p=0.031, Student's t-test) was observed, but no change in amplitude (16.55±1.490 pA, dark vs 17.76±2.13 pA, light) of AMPA mEPSCs was detected (FIG. 2C). sPA-BoNT$_{milli}$ was not as effective at impairing mEPSCs in cultured hippocampal neurons, presumably due to lower expression levels of virally-delivered sPA-BoNT. Together, these results demonstrated that sPA-BoNT$_{milli}$ effectively cleaves VAMP2 and impairs neurotransmission, although with relatively slow kinetics.

Example 3: Targeting Split BoNT/B to Synaptic Vesicles Enhances Kinetics and Potency of PA-BoNT Next it was tested whether targeting PA-BoNT to synaptic vesicles increases its efficacy. The BoNT(N)-iLID fragment was fused to the synaptic vesicle protein synaptophysin (syph) along with a EGFP reporter (FIG. 3A). The SspB-fused BoNT(C) fragment (SspB$_{micro}$ or SspB$_{milli}$) was expressed separately as a soluble protein. Thus light will trigger protease assembly directly on synaptic vesicles, in close proximity to VAMP2. This combination is referred to herein as vesicular PA-BoNT (vPA-BoNT). A 3-fold increase was observed in the rate of VAMP2 cleavage using vPA-BoNT$_{micro}$ compared to the soluble sPA-BoNT (vPA-BoNT τ=7±2 min vs. sPA-BoNT τ=21±4 min; FIG. 3B). Importantly, vPA-BoNT$_{micro}$ showed an increased maximal fraction of VAMP2 cleavage in light compared to sPA-BoNT$_{micro}$ (90±5% vPA-BoNT$_{micro}$ vs 65±4%, sPA-BoNT$_{micro}$) (FIG. 2B; FIG. 3B). vPA-BoNT was similarly active when the C-terminal BoNT/B fragment was anchored to vesicles as a synaptophysin fusion (i.e., syphGFP-SspB-BoNT(C)+BoNT(N)-iLID) and/or when SspB$_{milli}$ was used (FIGS. 8A-8D).

Figures 3E, 3F:
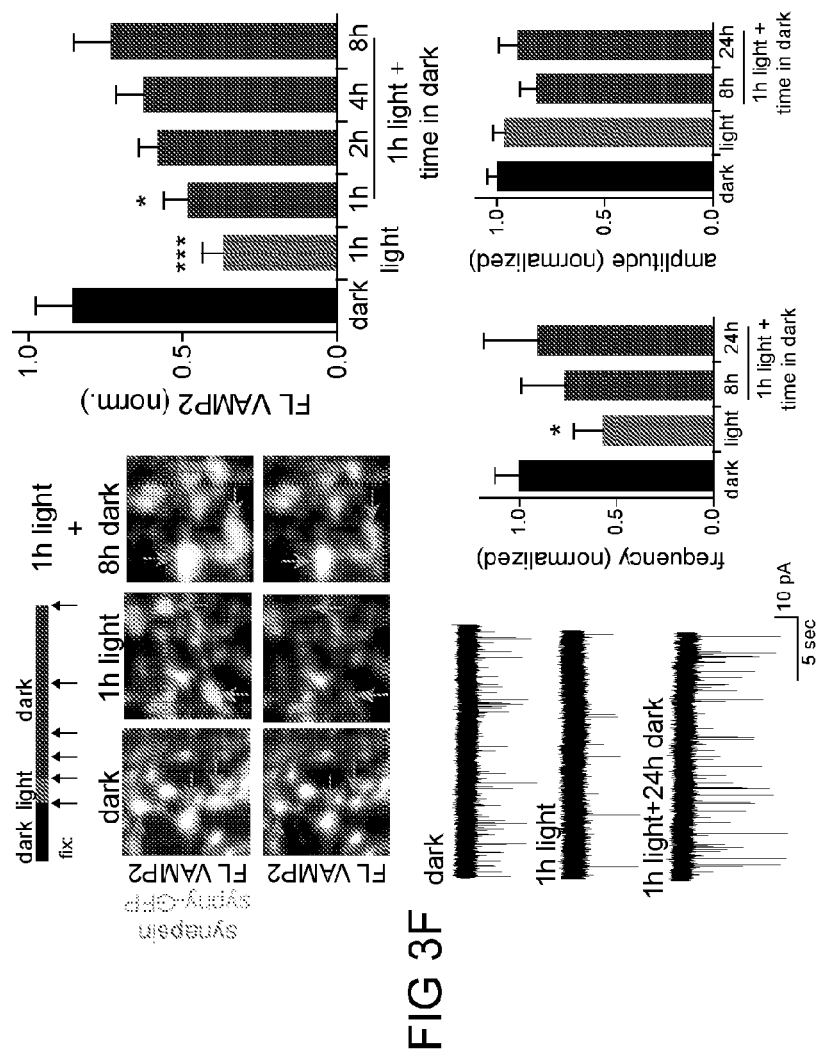
FIG. 3F shows a timecourse of functional recovery in neurons. Cultured neurons infected with vPA-BoNT were treated with 1 h of blue light and mEPSC frequency and amplitude were measured immediately following light exposure or following 8h or 24h of dark recovery. Data are normalized to neurons expressing vPA-BoNT but maintained in darkness for the duration of the experiment.

Given its robust light-dependent VAMP2 cleavage, vPA-BoNTmicro was functionally characterized. Spontaneous quantal neurotransmitter release was first measured by recording AMPA receptor mediated mEPSCs in dissociated hippocampal cultures that had been infected with AAVs encoding vPA-BoNT. Neurons expressing the toxin constructs displayed a slight increase in frequency, but not amplitude of mEPSCs. Subsequent light exposure resulted in a 2-fold decrease in mEPSC frequency, compared to neurons kept in the dark for the duration of the experiment (FIGS. 3C, 3D). Next, the duration for synaptic transmission to recover following vPA-BoNT activation was quantified by measuring VAMP2 protein levels and recording mEPSCs at various dark recovery times (FIG. 3E-3F). 8h following light exposure, VAMP2 protein levels had nearly recovered to dark control levels (FIG. 3E). mEPSC frequency was reduced at 8 h and required 24h for full recovery (FIG. 3F).

The discrepancy between protein levels and function may be due to the population of vesicles with crippled VAMP2 occluding newer vesicles containing intact VAMP2 from active zones. The reversal kinetics, which depend on synthesis and trafficking of new VAMP2 to synaptic sites, required several hours to one day.

To more precisely define the onset kinetics of the functional effects of vPA-BoNT, spontaneous quantal neurotransmission was monitored by imaging $Ca^{2+}$ influx through postsynaptic NMDA receptors at individual synapses using the red $Ca^{2+}$ indicator jRGECO1a. Dissociated hippocampal cultures infected with AAVs encoding vPA-BoNT were sparsely transfected with jRGECO1a and imaged in extracellular solution containing tetrodotoxin to block action potential-triggered vesicle fusion and lacking $Mg^{2+}$ to allow $Ca^{2+}$ entry through NMDA receptors upon glutamate binding. Under these conditions, robust spontaneous $Ca^{2+}$ transients could be observed at individual dendritic spines that report quantal glutamate release (FIG. 3G). This approach allowed measurement of spontaneous neurotransmission longitudinally, at the same synapses over much longer periods of time than is possible with whole cell recordings. Under baseline conditions no difference was observed between the average number of postsynaptic $Ca^{2+}$ transients at single synapses in cultures infected with AAVs encoding vPA-BoNT (but not exposed to blue light) compared to uninfected cultures (uninfected: 6.3±04 events/synapse/min vs. infected dark: 6.3±0.3 events/synapse/min) (FIG. 3H). Subsequent blue light treatment suppressed the frequency, but not the amplitude of spontaneous $Ca^{2+}$ transients with similar kinetics to VAMP2 cleavage measured by immunocytochemistry (FIGS. 3H,3I). Nearly identical results were observed upon swapping the component of PA-BoNT that was tethered to vesicles (i.e. syphGFP-SspB-BoNT(C)+BoNT(N)-iLID) and/or used $SspB_{milli}$ (FIG. 8A-D). Finally, local activation of vPA-BoNT with subcellular spatial resolution was tested. Baseline synaptic $Ca^{2+}$ transients were imaged at the same synapses before and after local illumination of a sub-region of the dendritic arbor (FIG. 3J). Synapses within the illuminated region displayed a robust decrease in frequency, but not amplitude of postsynaptic $Ca^{2+}$ transients, compared with unilluminated synapses on the same neurons or illuminated control cells from cultures not expressing vPA-BoNT (FIGS. 3K, 3L). Thus, vPA-BoNT activation could be targeted to user-defined presynaptic inputs.

Figure 4A:
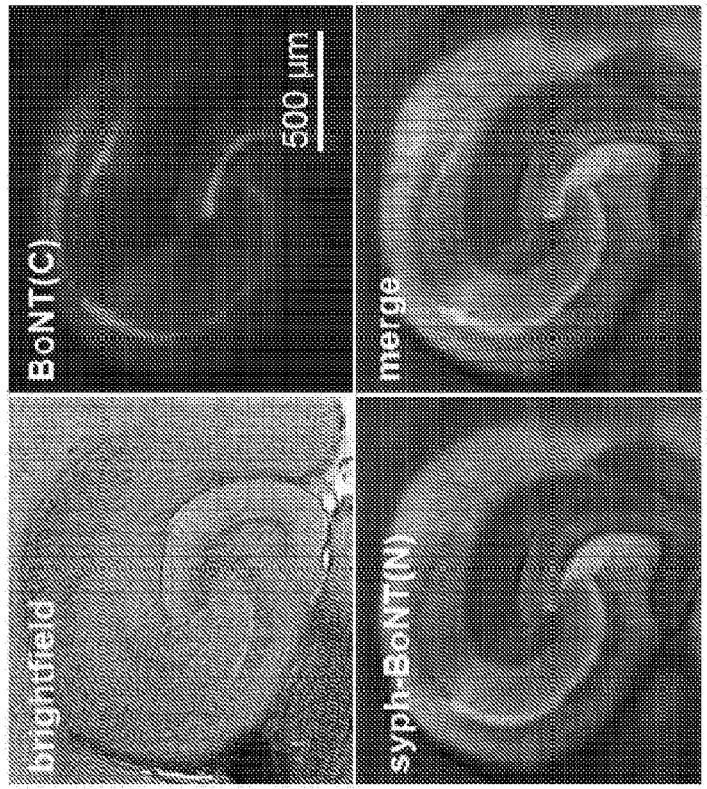
FIGS. 4A-4H illustrate vPA-BoNT for regulating excitatory neurotransmission in an intact circuit.
Figure 4B:
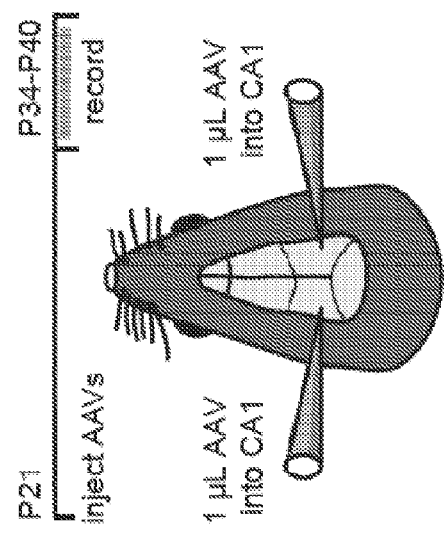
Figure 4C:
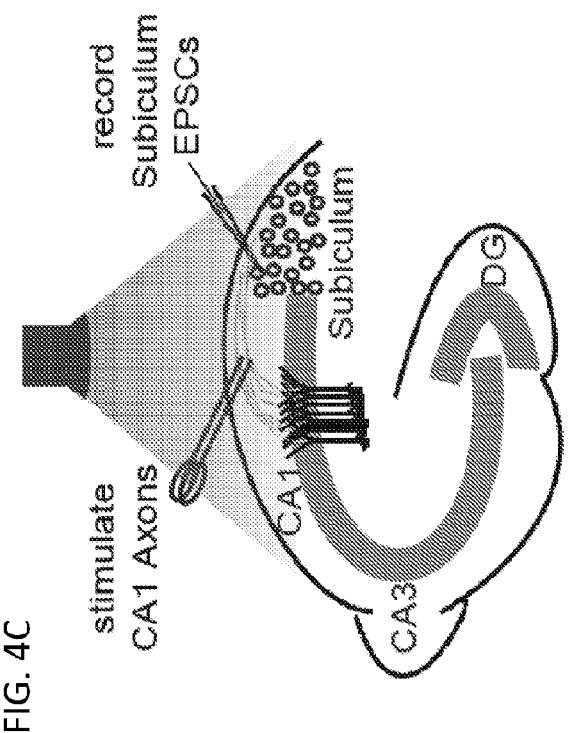
Figure 4D:
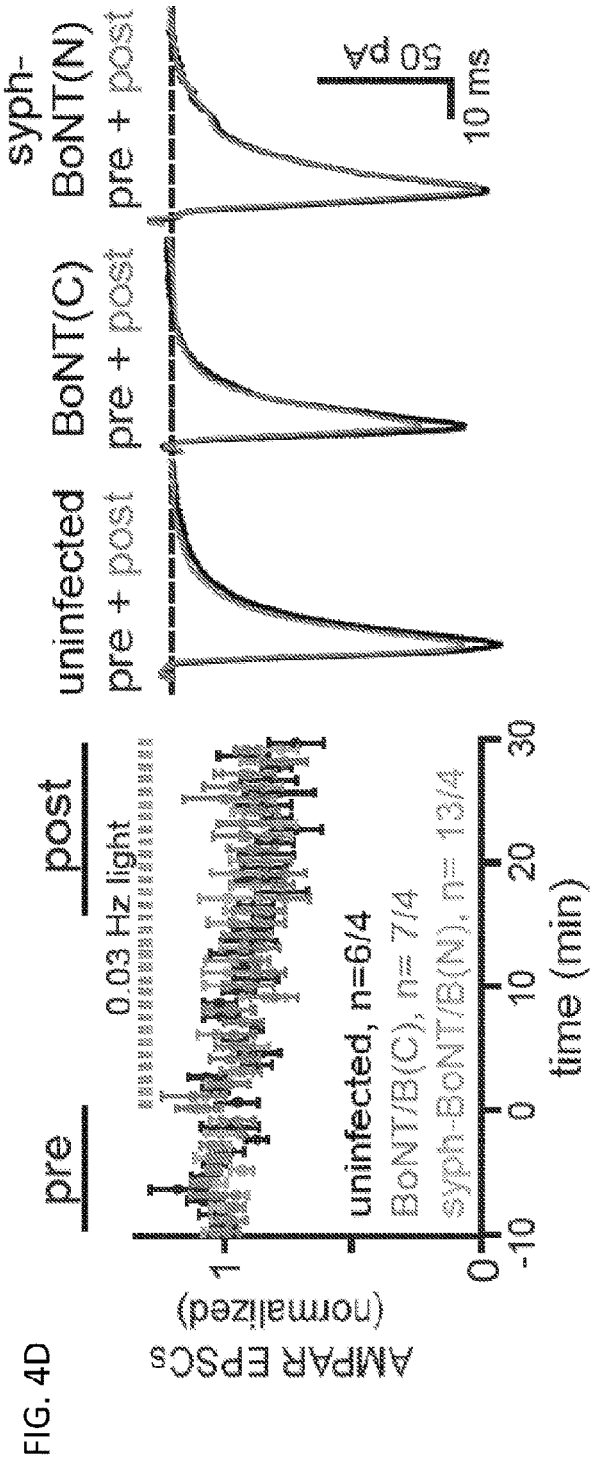
Figure 4E:
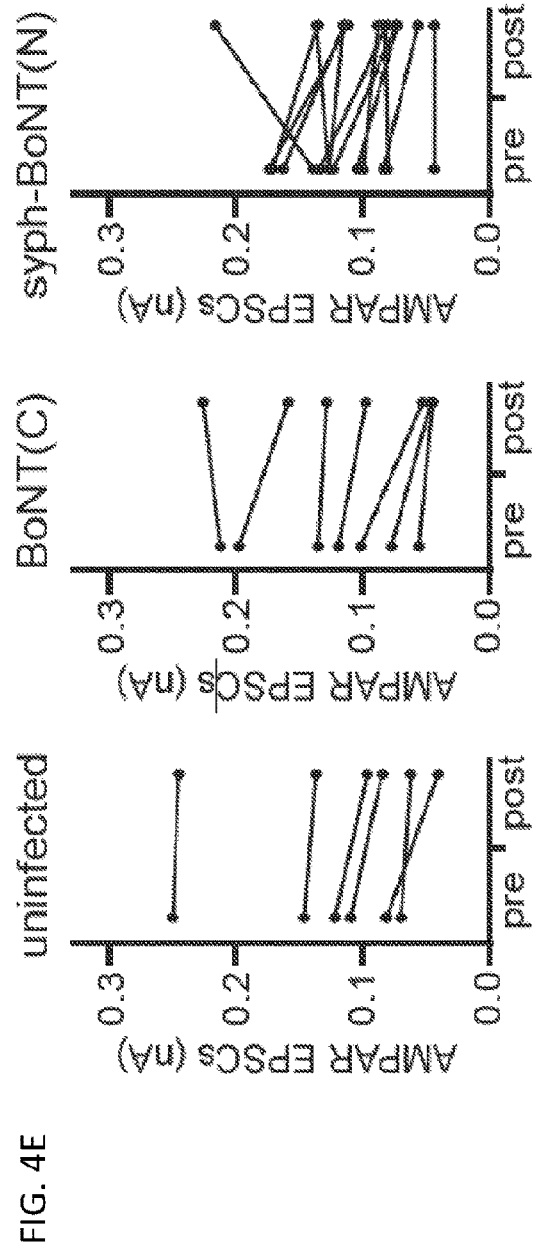
Figure 4F:
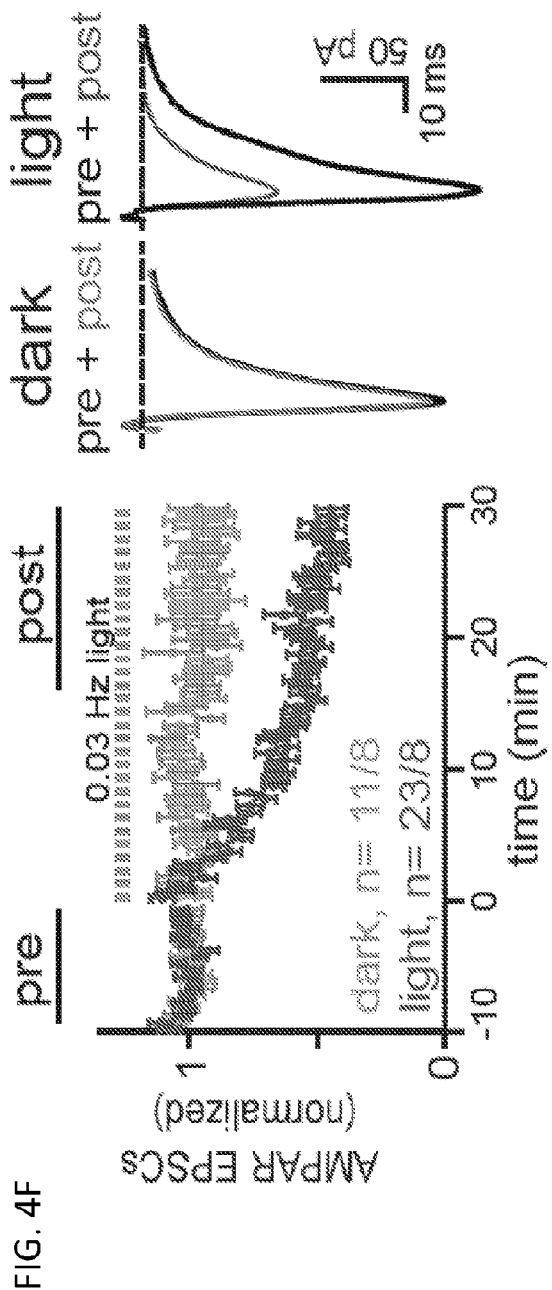
Figure 4G:
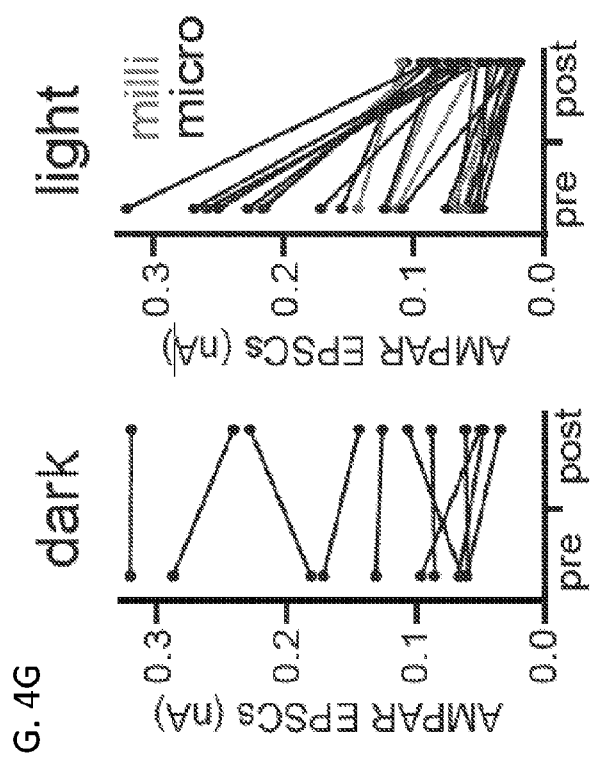
Figure 4H:
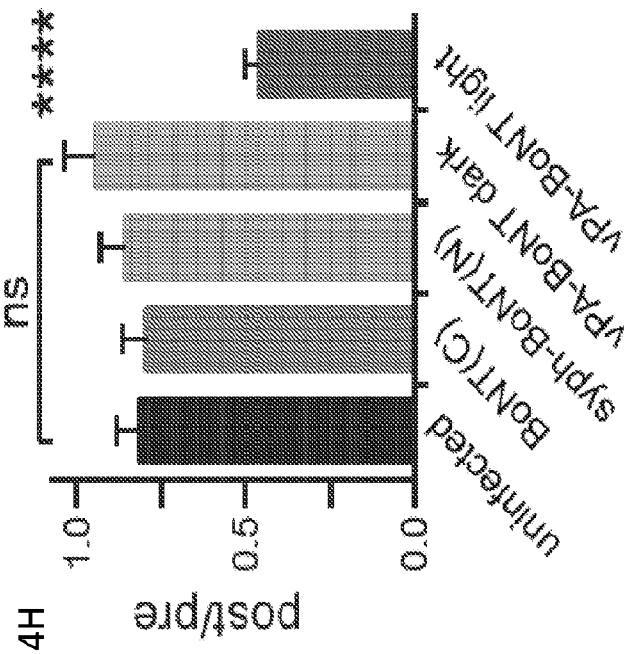

Example 4: vPA-BoNT/B is Effective for Regulating Excitatory Neurotransmission in Intact Circuits Following validation in dissociated hippocampal neurons, it was tested whether vPA-BoNT can be used for controlling neurotransmission in an intact circuit. Hippocampal CA1 pyramidal neurons project to the subiculum, providing an ideal circuit to test the effectiveness of vPA-BoNT for disrupting presynaptic neurotransmitter release. Two AAVs, each encoding one of the vPA-BoNT fragments, were co-injected into hippocampal CA1 region (FIG. 4A). Acute slices were prepared 1.5-2 weeks following injection and expression was verified by fluorescent reporters engineered into the constructs (FIG. 4B). Whole cell voltage clamp recordings of AMPA receptor EPSCs were made from primary subicular neurons visually confirmed to be uninfected by either virus (FIG. 4C). After establishing baseline EPSC amplitude, the slices were exposed to blue light pulses for 30 minutes. A robust reduction was observed in EPSC amplitude coincident with the onset of blue light exposure (FIGS. 4D-4G). Slices from animals infected with vPA-BoNT but not exposed to blue light, or uninfected slices that were exposed to blue light, showed only a mild run-down (10±6%) over the same time period. Neither fragment expressed on its own was sufficient to disrupt neurotransmission (FIG. 4D; FIG. 4E; FIG. 4H). Nearly identical results were obtained using $SspB_{milli}$ or $SspB_{micro}$ as the iLID dimerizer (FIG. 4G).

While vPA-BoNT robustly inhibited neurotransmission in this circuit, it was not completely eliminated. Residual neurotransmission could arise from incomplete block of vesicular release. Alternately, it is possible that a subset of presynaptic inputs did not express vPA-BoNT. To discriminate between these possibilities, presynaptic release probability (Pr) was estimated using a paired-pulse paradigm. It was reasoned that if neurotransmission was efficiently blocked in vPA-BoNT neurons, but uninfected neurons contributed to residual neurotransmission, Pr would not change when measured before and after light exposure. Alternatively, if most stimulated inputs expressed PA-BoNT but were only partially blocked, decreased Pr following light exposure would be observed. No significant change was observed in Pr from baseline levels following 30 minutes of blue light exposure (FIGS. 9A-9B). This observation is consistent with robust impairment of neurotransmission in vPA-BoNT-expressing neurons with residual transmission arising from presynaptic input from uninfected neurons. Importantly, expression of vPA-BoNT did not influence Pr on its own, when compared to uninfected controls (FIG. 9C). Together these results confirm that vPA-BoNT/B can be used to acutely disrupt excitatory neurotransmission in intact circuits.

Example 5: BoNT/B Light Chain can be Functionally Reconstituted from Fragments

Figure 10A:
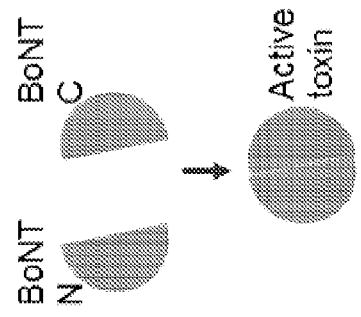
FIG. 10A is a schematic showing that the light chain of BoNT A or B can be split into two fragments and reconstitute to regain function.
Figure 10B:
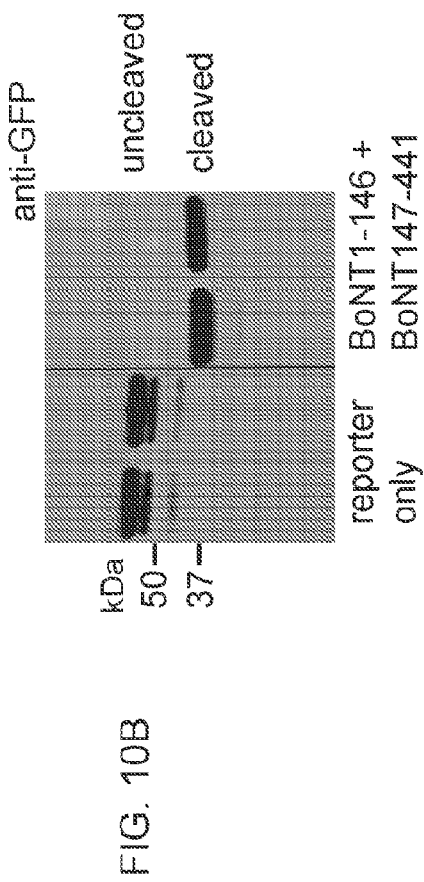
FIG. 10B illustrates the finding that BoNT/B N-terminal and C-terminal fragments, split at residue 146/147, can self-associate on their own. HEK293T cells were transfected with either a GFP-VAMP-GST cleavage reporter alone, or the GFP-VAMP-GST reporter along with BoNT/B N- and C-terminal fragments split at residue 146/147. Twenty-four hours post transfection, cells were treated with 461 nm blue light (2s pulse every 3 min) or kept in dark for 5 hrs, then analyzed by immunoblot for reporter cleavage, using an anti-GFP antibody.

It was tested whether BoNT/B light chain could be split into two fragments and functionally reconstituted. BoNT/B LC was split into a N-terminal fragment, consisting of residues 1-146, and a C-terminal fragment, consisting of residues 147-441. When both fragments were coexpressed with a GFP-VAMP-GST reporter that is cleaved by BoNT/B, 100% of the GFP-VAMP-GST reporter was cleaved (FIG. 10B). These results show that BoNT/B can be expressed in fragments that can be reconstituted together to result in activity.

Example 6: BoNT/A Light Chain can be Functionally Reconstituted from Fragments

Figure 10C:
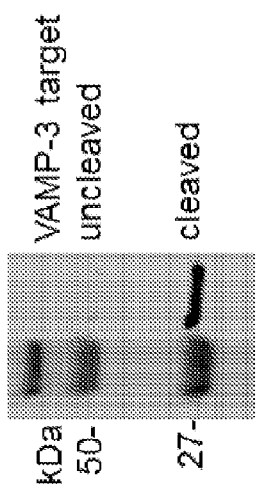
FIG. 10C demonstrates reconstitution of activity of BoNT/A light chain that has been split into two fragments. BoNT/A was split into two fragments that were fused to dimerizers that associate with high affinity in light and dark (BoNT/A residues 1-203 fused to iLID V416I; BoNT/A residues 204-448 fused to SspB wild-type). Reconstitution of activity was monitored by quantifying cleavage of a VAMP-3 reporter (uncleaved, 50 kD; cleaved, 27 kDa).
Figure 11:
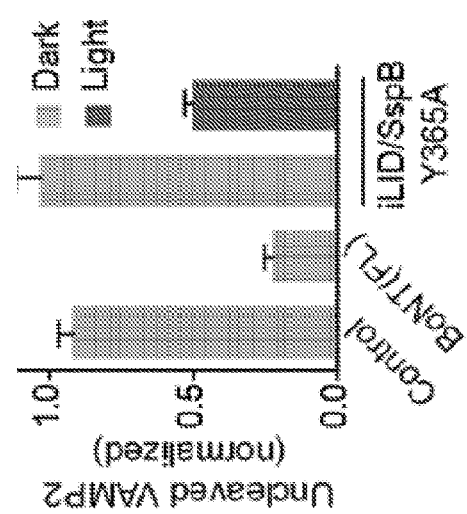
FIG. 11 illustrates that light exposure activates BoNT in cell culture as measured by VAMP2 cleavage. The antibody used only recognizes full length VAMP2, so cleavage is represented by the loss of staining.

BoNT/A light chain was split into a N-terminal fragment, consisting of residues 1-203, and a C-terminal fragment, consisting of residues 204-441. The N-terminal BoNT fragment was fused to iLID (SEQ ID NO:5) (V416I) at the C-terminus, while the C-terminal BoNT fragment was fused to wild-type SspB domain (SEQ ID NO:6). When coexpressed in cells with a GFP-VAMP3-GST reporter 95-100% of the reporter was cleaved (FIG. 10C). These results show that BoNT/A can be expressed in fragments that can be reconstituted together to result in activity.

Example 7

The present study describes the development of a first-in-class optogenetic tool, PA-BoNT, for light-triggered synaptic silencing. Related methods to date lack spatial and temporal precision and control and some can have off-target effects that can affect neuronal physiology in unexpected ways. PA-BoNT overcomes many limitations of the existing technologies as it acts through a defined mechanism (cleavage of VAMP proteins) and requires only brief light exposure. Another advantage is that PA-BoNT activity can be monitored using the commonly available antibody used in this example that does not recognize VAMP2 BoNT/B cleavage products. Thus, post-hoc immunohistochemistry can be used to precisely calibrate toxin activity under different illumination conditions and to define the anatomic region of activation. Together, these features make PA-BoNT a unique and powerful silencing approach that fills a substantial gap in the current optogenetic toolkit for spatially restricted, long-term silencing.

In certain embodiments, the two-component AAV system used herein is advantageous for manipulating genetically intractable neural subtypes using intersectional approaches, or for manipulating specific projections by introducing one of the fragments in a retrograde trafficking virus injected at the target site. Finally, persistent synapse silencing comes at the cost of rapid reversibility. Because BoNT/B cleaves VAMP proteins, recovery of synaptic transmission depends either on synthesis of new VAMP proteins (if the entire neuron was illuminated), or on lateral trafficking of uncleaved VAMP proteins to the inactivated region from non-illuminated synaptic sites or the cell body.

It was demonstrated herein that simply targeting PA-BoNT to synaptic vesicles greatly enhances its ability to silence neurotransmitter release. Indeed, this strategy allows for potent and selective disruption of different secretory molecules released from the same cell. In principle, PA-BoNT can be targeted to selectively disrupt one class of neurotransmitter. In addition to neurotransmitter release, the mechanism of regulated secretion targeted by BoNT is important for a wide range of biological functions. PA-BoNT can also be used to conditionally disrupt secretion of diverse biomolecules from numerous cell types, including neuroendocrine cells, pancreatic cells, immune cells and glia. In addition to systems—level applications, this tool is useful for advancing the understanding of the molecular mechanisms of vesicular fusion. The ability to rapidly disrupt SNARE proteins will help elucidate the machinery responsible for priming, docking and fusion of secretory vesicles in diverse cell types whose fusion mechanisms remain obscure or controversial.

Finally, because the *botulinum* toxin protein family is structurally conserved, engineering efforts for BoNT/B are broadly applicable to related toxins with distinct substrate specificities, including other BoNT serotypes. In addition to engineering conditional versions of toxins that act on different endogenous substrates, coevolution of orthogonal protease/substrate pairs can lead to novel light-dependent protease systems that expand our ability to precisely manipulate cellular systems in space and time.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. Although this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A light-controlled protein system comprising:
a first construct comprising a first fragment of a protein comprising the first fragment and a second fragment, wherein the first fragment is fused to a first photodimerizer molecule; and
a second construct comprising the second fragment of the protein, wherein the second fragment is fused to a second photodimerizer molecule;
wherein the protein is a *Clostridium botulinum* neurotoxin serotype B (BoNT/B), or a biologically active fragment thereof;
wherein, in the absence of visible light, the first photodimerizer molecule does not bind to the second photodimerizer molecule, forming a non-activated system;
wherein, in the presence of visible light, the first photodimerizer molecule binds to the second photodimerizer molecule, thus promoting physical contact between the first fragment of the protein and the second fragment of the protein, and forming an activated system;
wherein the biological activity of the protein in the activated system is higher than in the non-activated system; and
wherein
the first fragment comprises amino acid residues 1-146 of SEQ ID NO:4, and the second fragment comprises amino acid residues 147-441 of SEQ ID NO:4, or
the first fragment comprises amino acid residues 1-146 of SEQ ID NO:4, the second fragment comprises amino acid residues 147-441 of SEQ ID NO:4, and the second fragment has at least one mutation selected from the group consisting of K94A, N157A, Y365A, and S311A/D312A in the corresponding residues of SEQ ID NO: 4.

2. The system of claim 1, wherein the visible light is blue light.

3. The system of claim 1, wherein the first fragment of the protein comprises an N-terminal portion of the BoNT/B light chain, and wherein the second fragment of the protein comprises a C-terminal portion of the BoNT/B light chain.

4. The system of claim 1, wherein either:
(a) the first photodimerizer molecule comprises a cryptochrome 2 (CRY2) molecule, and the second photodimerizer molecule comprises CIBN; or
(b) the first photodimerizer molecule comprises a LOV domain-peptide fusion (iLID), and the second photodimerizer molecule comprises a domain of *E. coli* SspB.

5. The system of claim 4, wherein at least one of following applies:
(a) the iLID has a V416I mutation; and
(b) the SspB comprises SspB$_{milli}$.

6. The system of claim 1, further comprising a synaptic vesicle protein synaptophysin (Syph) fused to the first construct or the second construct.

7. A composition comprising a first adeno-associated viral (AAV) vector comprising a nucleotide sequence encoding the amino acid sequence of a first construct, and a second AAV vector comprising a nucleotide sequence encoding the amino acid sequence of a second construct,
wherein the first construct comprises a first fragment of a protein comprising the first fragment and a second fragment, and the first fragment is fused to a first photodimerizer molecule;
wherein the second construct comprises the second fragment of the protein, wherein the second fragment is fused to a second photodimerizer molecule; and
wherein
the first fragment comprises amino acid residues 1-146 of SEQ ID NO:4, and the second fragment comprises amino acid residues 147-441 of SEQ ID NO:4, or
the first fragment comprises amino acid residues 1-146 of SEQ ID NO:4, the second fragment comprises amino acid residues 147-441 of SEQ ID NO:4, and the second fragment has at least one mutation selected from the group consisting of K94A, N157A, Y365A, and S311A/D312A in the corresponding residues of SEQ ID NO: 4.

8. The composition of claim 7, wherein the first fragment comprises an N-terminal portion of the BoNT/B light chain, and wherein the second fragment comprises a C-terminal portion of the BoNT/B light chain.

9. The composition of claim 7, wherein either:
(a) the first photodimerizer molecule comprises a cryptochrome 2 (CRY2) molecule, and the second photodimerizer molecule comprises CIBN; or
(b) the first photodimerizer molecule comprises a LOV domain-peptide fusion (iLID), and the second photodimerizer comprises a domain of *E. coli* SspB.

10. The composition of claim 9, wherein at least one of the following applies:
(a) the iLID has a V416I mutation; and
(b) the SspB comprises SspB$_{milli}$.

11. The composition of claim 7, wherein the first construct or the second construct is further fused to a synaptic vesicle protein synaptophysin (Syph).

12. A method for preparing a BoNT/B protein comprising BoNT/B activity or a BoNT/A protein comprising BoNT/A activity, the method comprising
providing a first BoNT/B light chain fragment comprising amino acid residues 1-146 of SEQ ID NO:4 or a first BoNT/A light chain fragment comprising amino acid residues 1-203 of SEQ ID NO:9;
providing a second BoNT/B light chain fragment comprising amino acid residues 147-441 of SEQ ID NO:4 or a second BoNT/A light chain fragment comprising amino acid residues 204-448 of SEQ ID NO:9, and
contacting the first BoNT/B light chain fragment with the second BoNT/B light chain fragment, whereby the first BoNT/B light chain fragment interacts with the second BoNT/B light chain fragment to reconstitute the BoNT/B protein comprising BoNT/B activity, or contacting the first BoNT/A light chain fragment with the second BoNT/A light chain fragment, whereby the first BoNT/A light chain fragment interacts with the second BoNT/A light chain fragment to reconstitute the BoNT/A protein comprising BoNT/A activity.

13. A composition comprising one of the following:
(a) a first BoNT/B light chain fragment comprising amino acid residues 1-146 of SEQ ID NO:4 and a second BoNT/B light chain fragment comprising amino acid residues 147-441 of SEQ ID NO:4, wherein the first BoNT/B light chain fragment further comprises a LOV domain-peptide fusion (iLID), and the second BoNT/B light chain fragment further comprises a wild-type SspB domain, or
(b) a first BoNT/A light chain fragment comprising amino acid residues 1-203 of SEQ ID NO: 9 and a second BoNT/A light chain fragment comprising amino acid residues 204-448 of SEQ ID NO:9, wherein the first BoNT/A light chain fragment further comprises a LOV domain-peptide fusion (iLID), and the second BoNT/A light chain fragment further comprises a wild-type SspB domain.

\* \* \* \* \*